US012256920B2

(12) United States Patent  
Epstein et al.

(10) Patent No.: US 12,256,920 B2  
(45) Date of Patent: Mar. 25, 2025

(54) PURSE-STRING SUTURES

(71) Applicant: Edwards Lifesciences Corporation, Irvine, CA (US)

(72) Inventors: Stephen Epstein, Baltimore, MD (US); John Richard Carpenter, Santa Ana, CA (US); Felino V. Cortez, Jr., Bowie, MD (US); Stephen Cournane, Severn, MD (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 456 days.

(21) Appl. No.: 17/657,326

(22) Filed: Mar. 30, 2022

(65) Prior Publication Data

US 2022/0218328 A1 Jul. 14, 2022

Related U.S. Application Data

(63) Continuation of application No. PCT/US2020/052398, filed on Sep. 24, 2020.

(60) Provisional application No. 63/012,030, filed on Apr. 17, 2020, provisional application No. 62/909,197, filed on Oct. 1, 2019.

(51) Int. Cl.  
*A61B 17/04* (2006.01)  
*A61B 17/11* (2006.01)

(52) U.S. Cl.  
CPC .......... *A61B 17/0401* (2013.01); *A61B 17/11* (2013.01); *A61B 2017/0406* (2013.01); *A61B 2017/1142* (2013.01)

(58) Field of Classification Search  
CPC ................ A61B 17/0401; A61B 17/11; A61B 2017/0406; A61B 2017/1142; A61B 17/0466; A61B 2017/00243; A61B 2017/00663; A61B 2017/0409; A61B 2017/0464; A61B 2017/0495; A61B 2017/06057; A61B 2017/0608; A61B 17/0057; A61F 2/2457  
USPC ....................................................... 606/232  
See application file for complete search history.

(56) References Cited

U.S. PATENT DOCUMENTS

| 10,285,569 B2 * | 5/2019 | Rohl .................. A61B 8/12 |
| 2003/0093117 A1 * | 5/2003 | Saadat .......... A61B 18/1442 |
| | | 606/221 |

(Continued)

FOREIGN PATENT DOCUMENTS

WO  WO-2010011777 A1 *  1/2010  ......... A61B 17/0057

*Primary Examiner* — Kathleen S Holwerda  
*Assistant Examiner* — Serenity A Miller  
(74) *Attorney, Agent, or Firm* — Carrie Zhang; Chang & Hale

(57) ABSTRACT

A method of suturing a tissue opening can comprise placing a tissue-facing surface of a first pad, a second pad and a third pad over respective tissue areas adjacent to the tissue opening. The second pad can be positioned on a first side of the first pad and the third pad can be positioned on a second side of the first pad. The first and second pads can be coupled to a suture, the suture forming a stitch over the upper surface of each of the respective pads. The suture can be stitched through an area of tissue between the first pad and the second pad, between the second pad and the third pad, and between the third pad and the first pad. A first distal portion and a second distal portion of the suture can be coupled to the third pad for forming the purse-string suture.

20 Claims, 19 Drawing Sheets

(56) References Cited

U.S. PATENT DOCUMENTS

2011/0028995 A1\* 2/2011 Miraki ............... A61B 17/0482
606/144
2019/0240023 A1\* 8/2019 Spence ................ A61F 2/2466

\* cited by examiner

1200

```
┌─────────────────────────────────────────────────────────────┐
│ THREAD FIRST SUTURE THROUGH FIRST LOCATION ON FIRST PAD     │ 1202
│ FROM LOWER SURFACE TO UPPER SURFACE OF FIRST PAD, AND       │
│ THREAD FIRST SUTURE THROUGH SECOND LOCATION ON FIRST        │
│ PAD FROM UPPER SURFACE TO LOWER SURFACE OF FIRST PAD        │
└─────────────────────────────────────────────────────────────┘
                              ↓
┌─────────────────────────────────────────────────────────────┐
│ POSITION FIRST PAD OVER TARGET TISSUE AT FIRST POSITION     │ 1204
│ ALONG FIRST PATH FOR FORMING FIRST PURSE-STRING SUTURE      │
│ AROUND OPENING IN TARGET TISSUE                             │
└─────────────────────────────────────────────────────────────┘
                              ↓
┌─────────────────────────────────────────────────────────────┐
│ THREAD FIRST SUTURE THROUGH TARGET TISSUE ALONG FIRST       │ 1206
│ PATH FROM FIRST POSITION ON FIRST PATH TO SECOND            │
│ POSITION ON FIRST PATH                                      │
└─────────────────────────────────────────────────────────────┘
                              ↓
┌─────────────────────────────────────────────────────────────┐
│ THREAD FIRST DISTAL PORTION OF FIRST SUTURE THROUGH         │ 1208
│ FIRST LOCATION ON SECOND PAD FROM LOWER SURFACE OF          │
│ SECOND PAD TO UPPER SURFACE OF SECOND PAD                   │
└─────────────────────────────────────────────────────────────┘
                              ↓
┌─────────────────────────────────────────────────────────────┐
│ THREAD SECOND DISTAL PORTION OF FIRST SUTURE THROUGH        │ 1210
│ SECOND LOCATION ON SECOND PAD FROM LOWER SURFACE            │
│ OF SECOND PAD TO UPPER SURFACE OF SECOND PAD                │
└─────────────────────────────────────────────────────────────┘
                              ↓
┌─────────────────────────────────────────────────────────────┐
│ POSITION SECOND PAD OVER TARGET TISSUE AT SECOND            │ 1212
│ POSITION ON FIRST PATH                                      │
└─────────────────────────────────────────────────────────────┘
                              ↓
```

```
         ↓
┌─────────────────────────────────────────────────────────────┐
│ THREAD SECOND SUTURE THROUGH FIRST LOCATION FROM            │
│ LOWER SURFACE TO UPPER SURFACE OF ONE OF FIRST PAD OR       │ 1214
│ SECOND PAD, AND THREAD SECOND SUTURE THROUGH                │
│ SECOND LOCATION FROM UPPER SURFACE TO LOWER SURFACE         │
│ OF ONE OF FIRST PAD OR SECOND PAD                           │
└─────────────────────────────────────────────────────────────┘
         ↓
┌─────────────────────────────────────────────────────────────┐
│ THREAD FIRST DISTAL PORTION OF SECOND SUTURE THROUGH        │
│ FIRST LOCATION FROM LOWER SURFACE TO UPPER SURFACE OF       │ 1216
│ OTHER OF FIRST PAD OR SECOND PAD AND THREAD SECOND          │
│ DISTAL PORTION OF SECOND SUTURE THROUGH SECOND              │
│ LOCATION FROM LOWER SURFACE TO UPPER SURFACE OF             │
│ OTHER OF FIRST PAD OR SECOND PAD                            │
└─────────────────────────────────────────────────────────────┘
         ↓
┌─────────────────────────────────────────────────────────────┐
│ TENSION FIRST SUTURE TO FORM FIRST PURSE-STRING SUTURE,     │ 1218
│ AND TENSION SECOND SUTURE TO FORM SECOND                    │
│ PURSE-STRING SUTURE                                         │
└─────────────────────────────────────────────────────────────┘
```

FIG. 12 (Cont.)

PURSE-STRING SUTURES

CROSS REFERENCE TO RELATED APPLICATIONS

This application is a continuation of International Patent Application No. PCT/US2020/052398, filed Sep. 24, 2020, which claims the benefit of U.S. Patent Application No. 63/012,030, filed Apr. 17, 2020, and the benefit of U.S. Patent Application No. 62/909,197, filed Oct. 1, 2019, the entire disclosures all of which are incorporated by reference for all purposes.

BACKGROUND

Field

The present disclosure generally relates to the field of suturing tissue openings.

Description of Related Art

Purse-string sutures can be stitched or placed around openings formed in various types of tissues for managing the openings, including to seal the openings. For example, purse-string sutures can be formed in heart tissue. In some cases, purse-string sutures can be used to manage openings formed on the heart wall during procedures for treating heart conditions.

SUMMARY

Described herein are methods and devices relating to purse-string sutures stitched or placed into a target tissue to close and/or seal an opening in the target tissue. The purse-string sutures can be formed in a heart wall, such as to close an opening in the heart wall formed to deploy one or more tethers to the mitral valve leaflet for coupling the leaflet to the heart wall. The purse-string sutures can enable extension of the tethers through the opening for coupling the tethers to the heart wall, without or substantially without undesired damage to the tethers.

In some implementations, a method of suturing a tissue opening can comprise placing a tissue-facing surface of a first pad over a first tissue area adjacent to the tissue opening in a target tissue, the first pad being coupled to a suture, the suture forming a first stitch over an upper surface of the first pad oriented away from the target tissue; placing a tissue-facing surface of a second pad over a second tissue area adjacent to the tissue opening on a first side of the first pad, the second pad being coupled to the suture, and the suture forming a second stitch over the upper surface of the second pad; and placing a tissue-facing surface of a third pad over a third tissue area adjacent to the tissue opening on a second side of the first pad, the third pad being coupled to the suture. The method can include stitching the suture through an area of tissue between the first pad and the second pad, through an area of tissue between the second pad and the third pad, and through an area of tissue between the third pad and the first pad. A first distal portion and a second distal portion of the suture can be coupled to the third pad for forming a purse-string suture.

In some instances, placing the tissue-facing surface of the first pad comprises aligning the first pad with a posterior mitral leaflet direction. In some instances, the target tissue is heart tissue and wherein placing the tissue-facing surface of the first pad comprises placing the first pad over a pericardium.

In some instances, distal ends of the first stitch and the second stitch are less than about 2 millimeters (mm) from respective nearest edges of the first pad and the second pad. In some instances, coupling the first distal portion and the second distal portion of the suture to the third pad comprises coupling the first and second distal portions to positions less than about 2 millimeters (mm) from nearest respective edges of the third pad.

In some instances, placing the tissue-facing surface of the first pad, placing the tissue-facing surface of the second pad, and placing the tissue-facing surface of the third pad comprises evenly distributing the first pad, second pad and third pad around the tissue opening.

In some implementations, a method of suturing an opening in a target tissue can comprise positioning a first pad over a target tissue at a first position on a first path for forming a first purse-string suture around the opening in the target tissue, the first pad being coupled to a first suture, wherein a first corresponding portion of the first suture is over an upper surface of the first pad, and wherein the upper surface of the first pad is configured to be oriented away from the target tissue. A first distal portion of the first suture and a second distal portion of the first suture can be coupled to a second pad, and the second pad can be positioned at a second position on the first path. The method can include providing a second suture coupled to one of the first pad and the second pad, the second suture for forming a second purse-string suture in the target tissue along a second path around and concentric with the first path, wherein a first corresponding portion of the second suture is over an upper surface of the one of the first pad and the second pad, and wherein the upper surface of the one of the first pad and the second pad is configured to be oriented away from the target tissue. A first distal portion of the second suture and a second distal portion of the second suture can be coupled to the other of the first pad and the second pad. The first distal portion and second distal portion of the first suture can be tensioned to form the first purse-string suture, and the first distal portion of the second suture and second distal portion of the second suture can be tensioned to form the second purse-string suture.

In some instances, ends of the first corresponding portion of the first suture positioned over the upper surface of the first pad are less than about 2 millimeters (mm) from respective nearest edges of the first pad. In some instances, coupling the first distal portion and the second distal portion of the first suture to the second pad comprises coupling the first distal portion and the second distal portion to respective locations on the second pad which are less than about 2 millimeters (mm) from respective nearest edges of the second pad. In some instances, distal ends of the first corresponding portion of the second suture positioned over the upper surface of the one of the first pad and the second pad are less than about 2 millimeters (mm) from respective nearest edges of the one of the first pad and the second pad. In some instances, coupling the first distal portion and the second distal portion of the second suture to the other of the first pad and the second pad comprises coupling the first distal portion and the second distal portion to respective locations on the other of the first pad and the second pad which are less than about 2 millimeters (mm) from respective nearest edges the first pad or the second pad.

In some instances, the target tissue is heart tissue and wherein positioning the first pad comprises positioning the first pad over a pericardium and at an apex region of a heart and aligning the first pad with a posterior mitral leaflet direction. In some instances, the first pad and the second pad each comprise a pledget.

In some instances, positioning the second pad comprises positioning the second pad at an opposing location from that of the first pad along the first path.

In some instances, the method can further comprise positioning a third pad over the target tissue at a third position on the first path, the third pad being coupled to the first suture and a third corresponding portion of the first suture being over an upper surface of the third pad, wherein the upper surface of the third pad is configured to be oriented away from the target tissue. In some instances, positioning the third pad over the target tissue at the third position comprises positioning the third pad between the first pad and the second pad. In some instances, positioning the first pad, positioning the second pad, and positioning the third pad comprises evenly distributing the first pad, the second pad, and the third pad around the opening in the target tissue along the first path. In some instances, distal ends of the third corresponding portion of the first suture positioned over the third pad are less than about 2 millimeters (mm) from respective nearest edges of the third pad.

In some instances, the method can further comprise coupling the second suture to the third pad, the second suture comprising a third corresponding portion positioned over the third pad, and the third corresponding portion of the second suture being parallel to the third corresponding portion of the first suture. In some instances, distal ends of the third corresponding portion of the second suture positioned over the third pad are less than about 2 millimeters (mm) from respective nearest edges of the third pad.

In some instances, the method can further comprise positioning a fourth pad over the target tissue at a fourth position on the first path, the fourth pad being coupled to the first suture and a fourth corresponding portion of the first suture being over an upper surface of the fourth pad, wherein the upper surface of the fourth pad is configured to be oriented away from the target tissue. In some instances, positioning the fourth pad over the target tissue at the fourth position comprises positioning the fourth pad between the third pad and the second pad.

In some instances, positioning the first pad, positioning the second pad, positioning the third pad, and positioning the fourth pad comprises evenly distributing the first pad, the second pad, the third pad and the fourth pad around the opening in the target tissue along the first path. In some instances, distal ends of the fourth corresponding portion of the first suture positioned over the fourth pad are less than about 2 millimeters (mm) from respective nearest edges of the fourth pad.

In some instances, the method can further comprise coupling the second suture to the fourth pad, the second suture comprising a fourth corresponding portion over the fourth pad. In some instances, distal ends of the fourth corresponding portion of the second suture over the fourth pad are less than about 2 millimeters (mm) from respective nearest edges of the fourth pad.

In some implementations, a method of suturing an opening in a target tissue can comprise threading a first suture through a first location on a first pad from a lower surface to an upper surface of the first pad, and threading the first suture through a second location on the first pad from the upper surface to the lower surface of the first pad, to position a first corresponding portion of the first suture over the upper surface of the first pad, the upper surface being configured to be oriented away from the target tissue. The method can include positioning the first pad over the target tissue at a first position along a first path for forming a first purse-string suture around the opening in the target tissue; and threading the first suture through the target tissue along the first path from the first position on the first path to a second position on the first path. A first distal portion of the first suture can be threaded through a first location on a second pad from a lower surface of the second pad to an upper surface of the second pad, wherein the lower surface is configured to be oriented toward the target tissue and the upper surface is configured to be oriented away from the target tissue. A second distal portion of the first suture can be threaded through a second location on the second pad from the lower surface of the second pad to the upper surface of the second pad. The method can include positioning the second pad over the target tissue at the second position on the first path; and threading a second suture through a first location from a lower surface to an upper surface of one of the first pad and the second pad, and threading the second suture through a second location from the upper surface to the lower surface of the one of the first pad and the second pad to position a first corresponding portion of the second suture over the upper surface of the one of the first pad and the second pad for forming a second purse-string suture around and concentric with the first purse-string suture, wherein the upper surface of the one of the first pad and the second pad is configured to be oriented away from the target tissue. The method can include threading a first distal portion of the second suture through a first location from a lower surface to an upper surface of the other of the first pad and the second pad and threading a second distal portion of the second suture through a second location from the lower surface to the upper surface of the other of the first pad and the second pad; and tensioning the first distal portion and the second distal portion of the first suture to form the first purse-string suture along the first path, and tensioning the first distal portion of the second suture and second distal portion of the second suture to form the second purse-string suture.

In some instances, the target tissue is heart tissue and wherein positioning the first pad comprises positioning the first pad over a pericardium and at an apex region of a heart and aligning the first pad with a posterior mitral leaflet. In some instances, the first pad and second pad each comprise a pledget.

In some instances, positioning the second pad comprises positioning the second pad at an opposing location on the first path relative to that of the first pad.

In some instances, threading the first suture through the first location on a first pad and threading the first suture through the second location on the first pad comprise threading the first suture through locations less than about 2 millimeters (mm) from respective nearest edges of the first pad, and wherein threading the second suture through the first location on the one of the first pad and the second pad and threading the second suture through the second location on the one of the first pad and the second pad comprise threading the second suture through locations less than about 2 millimeters (mm) from respective nearest edges of the one of the first pad and the second pad.

In some instances, threading the first distal portion of the first suture and threading the second distal portion of the first suture comprise threading the first and the second distal portions of the first suture through locations less than about 2 millimeters from respective nearest edges of the second pad, and wherein threading the first distal portion of the second suture and threading the second distal portion of the second suture comprise threading the first and the second distal portions of the second suture through locations less than about 2 millimeters from respective nearest edges of the other of the first pad and the second pad.

In some instances, the method can further comprise positioning a third pad between the first pad and the second pad. Positioning the third pad can comprise threading the first suture through the target tissue from the first position to a third position on the first path; threading the first suture through a first location on a third pad from a lower surface to an upper surface of the third pad, and threading the first suture through a second location on the third pad from the upper surface to the lower surface of the third pad, to position a third corresponding portion of the first suture over the upper surface of the third pad, the upper surface being configured to be oriented away from the target tissue; and positioning the third pad over the target tissue at the third position on the first path.

In some instances, positioning the first pad, positioning the second pad and positioning the third pad comprise evenly distributing the first pad, the second pad and the third pad along the first path around the opening in the target tissue.

In some instances, threading the first suture through the first location on the third pad and threading the first suture through the second location on the third pad comprise threading the first suture through locations less than about 2 millimeters (mm) from respective nearest edges of the third pad.

In some instances, further comprising threading the second suture through a third location from the lower surface to the upper surface of the third pad, and threading the second suture through a fourth location from the upper surface to the lower surface of the third pad to position a corresponding portion of the second suture over the upper surface of the third pad.

In some instances, the method can further comprise positioning a fourth pad between the third pad and the second pad, wherein positioning the fourth pad comprises: threading the first suture through the target tissue from the third position to a fourth position on the first path; threading the first suture through a first location on a fourth pad from a lower surface to an upper surface of the fourth pad, and threading the first suture through a second location on the fourth pad from the upper surface to the lower surface of the fourth pad, to position a fourth corresponding portion of the first suture over the upper surface of the fourth pad, the upper surface being configured to be oriented away from the target tissue; and positioning the fourth pad over the target tissue at the fourth position on the first path.

In some instances, positioning the first pad, positioning the second pad, positioning the third pad and positioning the fourth pad comprise evenly distributing the first pad, the second pad, the third pad, and the fourth pad along the first path around the opening in the target tissue.

In some instances, threading the first suture through the first location on the fourth pad and threading the first suture through the second location on the fourth pad comprise threading the first suture through locations less than about 2 millimeters (mm) from respective nearest edges of the fourth pad.

In some instances, the method can further comprise threading the second suture through a third location from the lower surface to the upper surface of the fourth pad, and threading the second suture through a fourth location from the upper surface to the lower surface of the fourth pad to position a corresponding portion of the second suture over the upper surface of the fourth pad.

In some implementations, a purse-string suture structure can comprise a first pad and a second pad positioned around an opening in a target tissue, the first pad and second pad each comprising an upper surface oriented away from the target tissue and a lower surface oriented toward the target tissue. The purse-string suture structure can comprise a first purse-string suture positioned around the opening in the target tissue and coupled to the first pad and the second pad, wherein the first purse-string suture comprises: a portion of the first purse-string suture positioned over the first pad, and distal portions of the first purse-string suture coupled to the second pad. The purse-string suture structure can comprise a second purse-string suture positioned around and concentric with the first purse-string suture, wherein the second purse-string suture is coupled to the first pad and the second pad, and the second purse-string suture comprises: a portion of the second purse-string suture positioned over one of the first pad and the second pad, and distal portions of the second purse-string suture coupled to the other of the first pad and the second pad.

In some instances, respective ends of the portion of the first purse-string suture positioned over the first pad are less than about 2 millimeters (mm) from respective nearest edges of the first pad and respective ends of the portion of the second purse-string suture positioned over one of the first pad and the second pad are less than about 2 millimeters (mm) from respective nearest edges of one of the first pad and the second pad. In some instances, distal portions of the first purse-string suture are coupled at positions less than about 2 millimeters (mm) from respective nearest edges of the second pad and distal portions of the first purse-string suture are coupled at positions less than about 2 millimeters (mm) from respective nearest edges of the other of the first pad and the second pad.

In some instances, the target tissue is heart tissue and wherein the first pad is aligned with a posterior mitral leaflet direction.

In some instances, the first pad and the second pad are at opposing locations around the tissue opening.

In some instances, the purse-string suture structure can further comprise a third pad positioned between the first pad and the second pad, wherein the first and second purse-string sutures are coupled to the third pad. In some instances, the purse-string suture structure can further comprise a fourth pad positioned around the opening, wherein the first and second purse-string sutures are coupled to the fourth pad.

Methods and structures disclosed herein for treating a patient also encompass analogous methods and structures performed on or placed on a simulated patient, which is useful, for example, for training; for demonstration; for procedure and/or device development; and the like. The simulated patient can be physical, virtual, or a combination of physical and virtual. A simulation can include a simulation of all or a portion of a patient, for example, an entire body, a portion of a body (e.g., thorax), a system (e.g., cardiovascular system), an organ (e.g., heart), or any combination thereof. Physical elements can be natural, including human or animal cadavers, or portions thereof; synthetic; or any combination of natural and synthetic. Virtual elements can be entirely in silica, or overlaid on one or more of the physical components. Virtual elements can be presented on any combination of screens, headsets, holographically, projected, loud speakers, headphones, pressure transducers, temperature transducers, or using any combination of suitable technologies.

For purposes of summarizing the disclosure, certain aspects, advantages and novel features have been described herein. It is to be understood that not necessarily all such advantages may be achieved in accordance with any particular instance. Thus, the disclosed instances may be carried out in a manner that achieves or optimizes one advantage or group of advantages as taught herein without necessarily achieving other advantages as may be taught or suggested herein.

BRIEF DESCRIPTION OF THE DRAWINGS

Various instances are depicted in the accompanying drawings for illustrative purposes and should in no way be interpreted as limiting the scope of the inventions. In addition, various features of different disclosed instances can be combined to form additional instances, which are part of this disclosure. Throughout the drawings, reference numbers may be reused to indicate correspondence between reference elements. However, it should be understood that the use of similar reference numbers in connection with multiple drawings does not necessarily imply similarity between respective instances associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some instances or configurations.

FIG. 12 is a flow diagram of another example of a process for forming two purse-string sutures around an opening in a target tissue, according to some instances.

DETAILED DESCRIPTION

Figure 1:
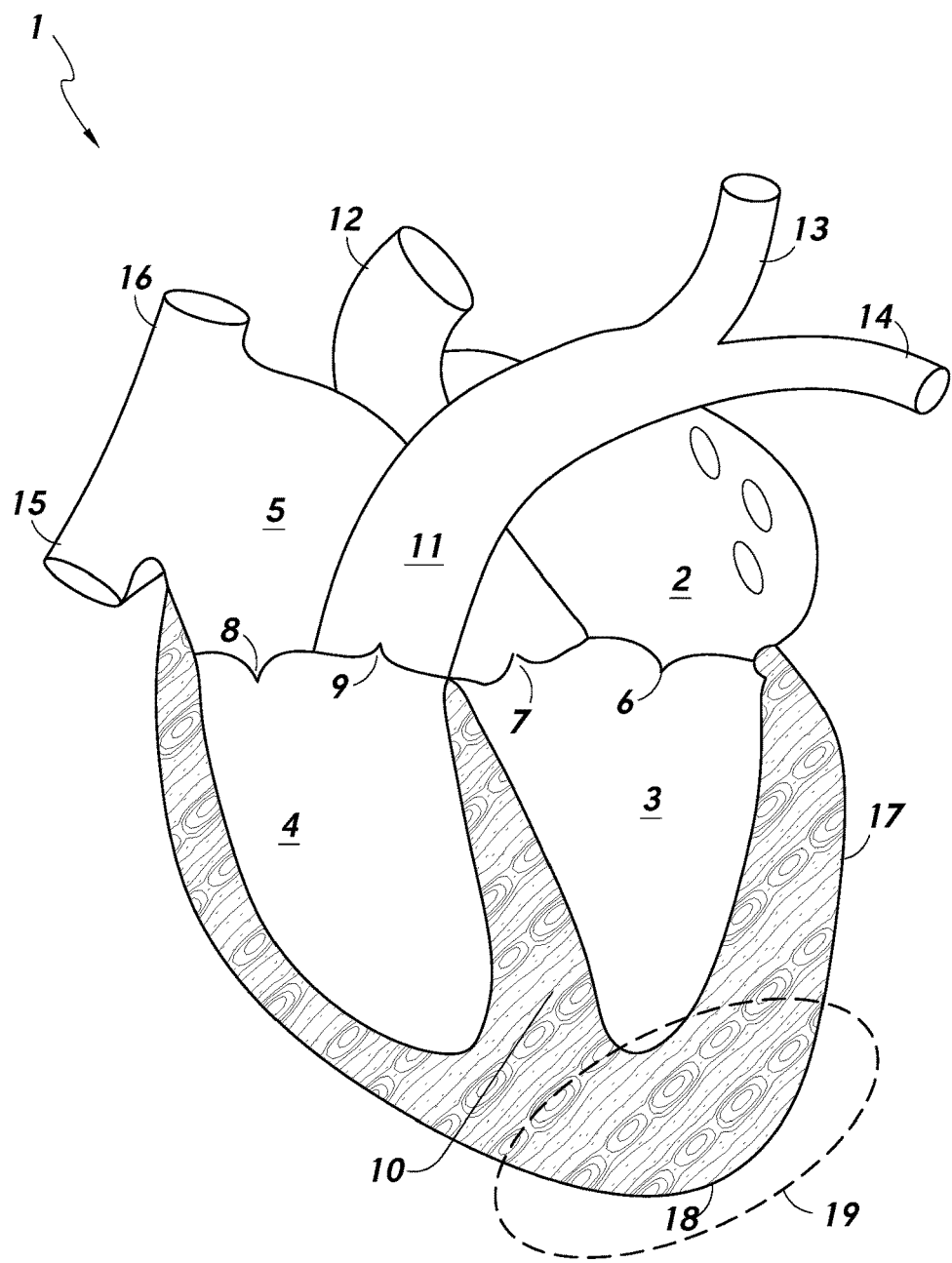
FIG. 1 is a cross-sectional view of a human heart.

The headings provided herein are for convenience only and do not necessarily affect the scope or meaning of the claimed invention.

The present disclosure relates to devices and methods related to improved purse-string sutures stitched around tissue openings, where the purse-string sutures can advantageously provide desired closure of the tissue openings while reducing or eliminating damage to any tethers extending through the closed opening.

Although certain preferred instances and examples are disclosed below, inventive subject matter extends beyond the specifically disclosed instances to other alternative instances and/or uses and to modifications and equivalents thereof. Thus, the scope of the claims that may arise herefrom is not limited by any of the particular instances described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain instances; however, the order of description should not be construed to imply that these operations are order dependent. Additionally, the structures, systems, and/or devices described herein may be embodied as integrated components or as separate components. For purposes of comparing various instances, certain aspects and advantages of these instances are described. Not necessarily all such aspects or advantages are achieved by any particular instance. Thus, for example, various instances may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred instances. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Purse-string sutures can be used for managing openings formed in various types of tissues. For example, a suture can be stitched through a target tissue along a path around an opening in the target tissue. The suture can subsequently be tensioned to form the purse-string suture around the opening. The suture can be tensioned such that the purse-string suture closes or reduces the size of the opening in the target tissue. The suture can be tensioned to seal the opening, and/or to close the opening around any instrumentation and/or material positioned in the opening. In some cases, purse-string sutures can be formed in heart tissue. For example, purse-string sutures can be stitched in a heart wall to close an opening formed in the heart wall, such as an opening formed in the heart wall in order to deliver medical device and/or therapy to a target site within the heart. Openings can be formed in the heart wall to treat various heart conditions. For example, the openings can be formed in the heart wall for various heart valve surgeries to treat any number of heart valve abnormalities, including to perform heart valve repair and/or replacement.

FIG. 1 is a schematic diagram showing various features of a human heart 1. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary trunk or artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary trunk 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets, such as due to prolapse of one or more of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Forming an opening through the heart wall 17 can be used to access a heart valve for treating various heart valve irregularities. Heart valve repair and/or replacement procedures can be performed to improve or restore valve function. For example, mitral valve repair procedures can be performed to alleviate mitral valve dysfunction, including mitral valve prolapse. In some cases, a transapical approach can be used to gain access into the heart 1. For example, mitral valve repair procedures can include accessing the mitral valve 6 from within the left ventricle 3, where entry into the left ventricle 3 can be achieved through the apex region 19 of the heart 1. The heart wall 17 can be punctured in the apex region 19 to form an opening so as to allow delivery of medical devices and/or therapy to the mitral valve 6. The apex region 19 is schematically shown in FIG. 1 as the area within the dashed circle. As used herein, the "apex region" can include the true apex 18 of the heart 1 and an area of the heart wall 17 covering up to about 5 centimeters (cm) around the true apex 18. For example, the opening in the left ventricular portion of the heart wall 17 about 2 centimeters (cm) to about 4 centimeters (cm) from the true apex 18.

Figure 2:
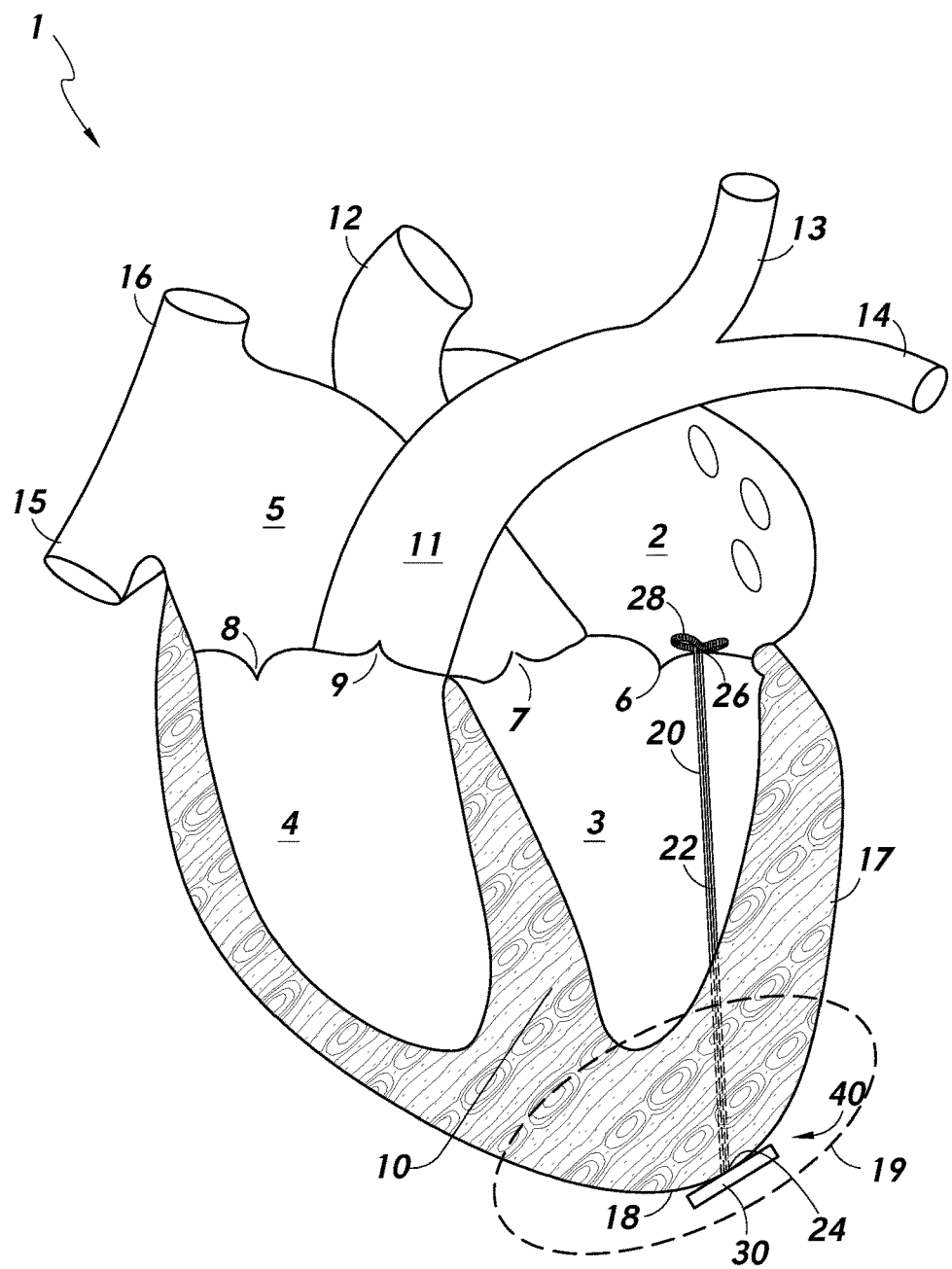
FIG. 2 is a cross-sectional view of the human heart and a tether coupling a mitral valve leaflet of the heart to a ventricular wall of the heart.

FIG. 2 schematically shows a tether 20 coupling a leaflet of the mitral valve 6 to the heart wall 17. Mitral valve repair surgeries can comprise deploying one or more tethers onto a mitral valve leaflet for tethering the leaflet to the heart wall 17. Coupling the leaflet to the heart wall 17 can facilitate reshaping of the mitral valve 6, such as to reduce or eliminate leaflet prolapse. The tether 20 can serve to improve coaptation of the leaflet. In some instances, the tether 20 can be configured to couple the leaflet to a left ventricular portion of the heart wall 17. In some instances, more than one tether can be used to couple the leaflet to the heart wall 17. These tethers can be made from a variety of materials. One or more of these tethers can comprise for example expanded polytetrafluoroethylene (ePTFE). For example, the tether 20 can be an ePTFE suture.

The tether 20 can comprise an elongate portion 22 which extends between a first end 24 and a second end 26. The first end 24 of the tether 20 can be coupled to the heart wall 17. The second end 26 of the tether 20 can be coupled to the leaflet of the mitral valve 6. In some instances, the second end 26 can comprise a suture knot 28 to facilitate securing the tether 20 to the leaflet. The suture knot 28 can be positioned at least partially over an upper surface of the leaflet. For example, the suture knot 28 can be positioned over an atrial facing surface of the mitral valve leaflet. The first end 24 can be anchored to a portion of the heart wall 17 at or proximate to the apex 18 of the heart 1, such as the apex region 19. In some instances, a portion of the elongate portion 22 can extend through the heart wall 17 such that the first end 24 is anchored at a position external to the heart 1. The first end 24 can be coupled to a pad 30 positioned on an exterior surface of the heart 1. For example, the pad 30 can be positioned over a pericardium of the heart 1. In some instances, the pad 30 can be positioned over an exterior surface of the heart 1 in the apex region 19. An opening 40 can be formed in the heart wall 17 to allow extension therethrough of the tether 20 such that the first end 24 of the tether 20 can be anchored to the pad 30. The opening 40 can be formed in the apex region 19 of the heart 1. The tether 20 can couple the mitral valve leaflet to the pad 30, extending from the leaflet through the left ventricle 3 and opening 40 in the heart wall 17 to the pad 30. The pad 30 can comprise any number of anchoring mechanisms configured to facilitate maintaining the first end 24 of the tether 20 anchored to the heart wall 17. In some instances, the pad 30 can comprise a pledget.

Figure 3:
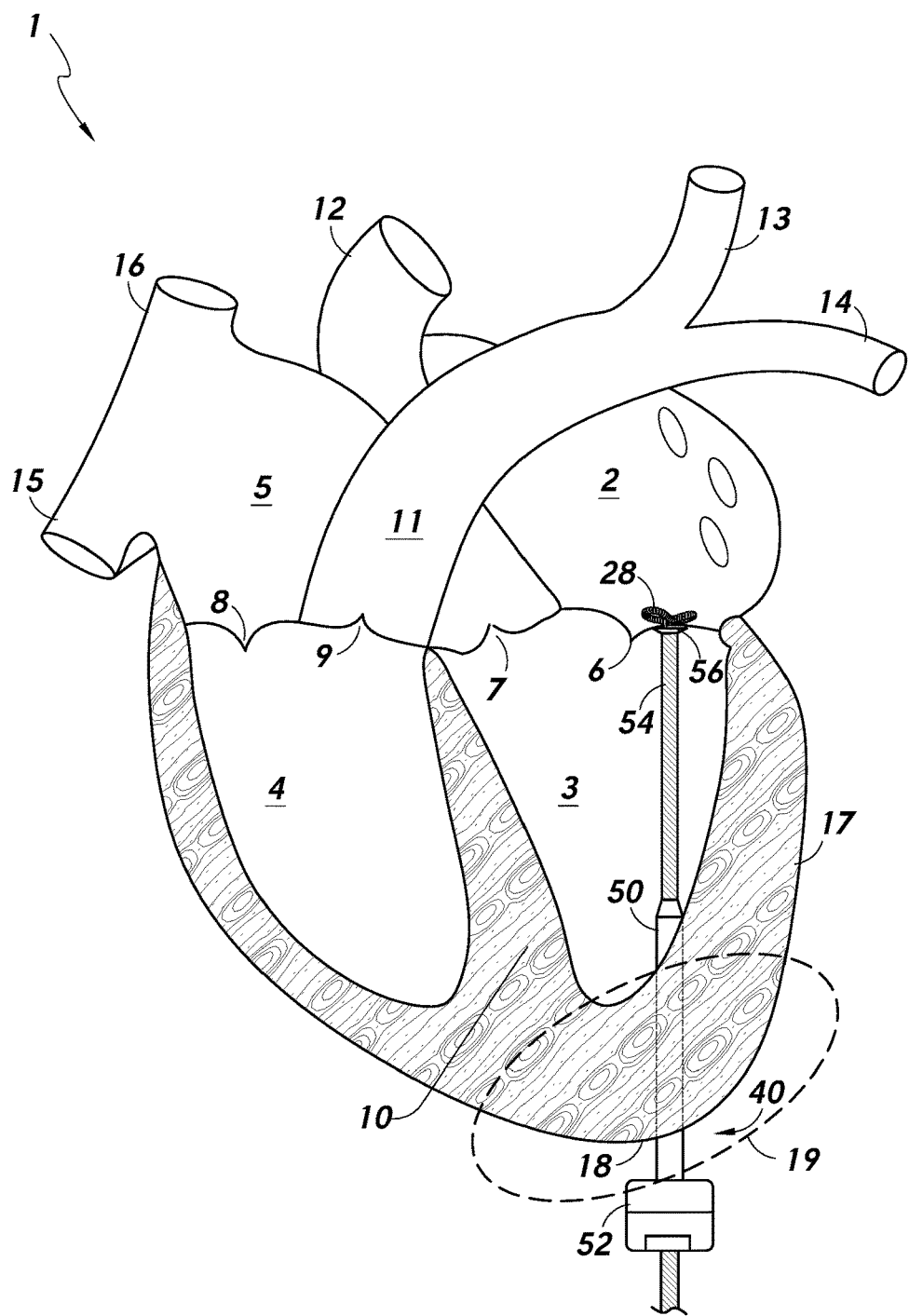
FIG. 3 is a cross-sectional view of the human heart and an introducer instrument configured to deploy the tether as described with reference to FIG. 2.

FIG. 3 shows a schematic diagram of an introducer instrument 50 positioned through the opening 40 formed in the heart wall 17 during a mitral valve repair procedure to facilitate deployment of the tether 20 to the mitral valve leaflet. The introducer instrument 50 can be configured to be positioned within and extending through the opening 40 during the procedure. The introducer instrument 50 can have a proximal portion 52 extending externally of the heart 1 to allow a user to control operation of the introducer instrument 50, and a distal portion 54 configured to be positioned within the heart 1. For example, the distal portion 54 can be positioned in the left ventricle 3 such that a distal end 56 of the introducer instrument 50 can be positioned proximate or adjacent to the mitral valve leaflet for deployment of the tether 20. In some instances, the second end 26 of the tether 20 can be deployed from the distal end 56 of the introducer instrument 50 to be positioned onto the mitral valve leaflet, positioning at least a portion of the suture knot 28 over the atrial facing surface of the leaflet. In some instances, the distal end 56 of the introducer instrument 50 can be positioned in contact with the mitral valve leaflet to facilitate deployment of the suture knot 28, including in contact with a ventricle facing surface of the leaflet.

One or more purse-string sutures can be stitched around the opening 40 formed in the heart wall 17. A purse-string suture can be formed in the target tissue to surround the opening 40 such that the purse-string suture can be tensioned to reduce the size of the opening 40 and/or to seal the opening 40. For example, a purse-string suture can be used to reduce the size of the opening 40 to close the opening 40 around any medical instruments extending through the opening 40 during a procedure, such as the introducer instrument 50. The purse-string suture can be closed around one or more medical instruments during a procedure to provide hemostasis. As described herein, more than one tether can be deployed to the mitral valve leaflet. For example, the purse-string suture can be closed around the introducer instrument 50 and one or more deployed tethers during a procedure, while one or more additional tethers are deployed using the introducer instrument 50. After completion of a procedure, the purse-string suture can be tensioned to seal the opening 40 in the heart wall 17. In some instances, the purse-string suture can be closed around one or more tethers after completion of a mitral valve repair procedure such that the opening 40 can be sealed around the one or more tethers.

Closing of openings sutured using traditional purse-string sutures can result in damage to portions of tethers extending therethrough. The traditional purse-string sutures can result in abrasive damage to and/or breakage of the tethers. Tensioning of traditional purse-string sutures, such as to close tissue openings around one or more tethers, can cause undesired folding of the tissue proximate and/or adjacent to the opening. The undesired folding of the tissue can in turn result in concentrated loading on portions of the tethers proximate to and/or extending through the opening, leading to damage and/or breakage of the tethers. A pattern of stitches used in traditional purse-string sutures can result in contact between the sutures and the one or more tethers, thereby contributing to damage and breakage of the tethers.

Figure 4:
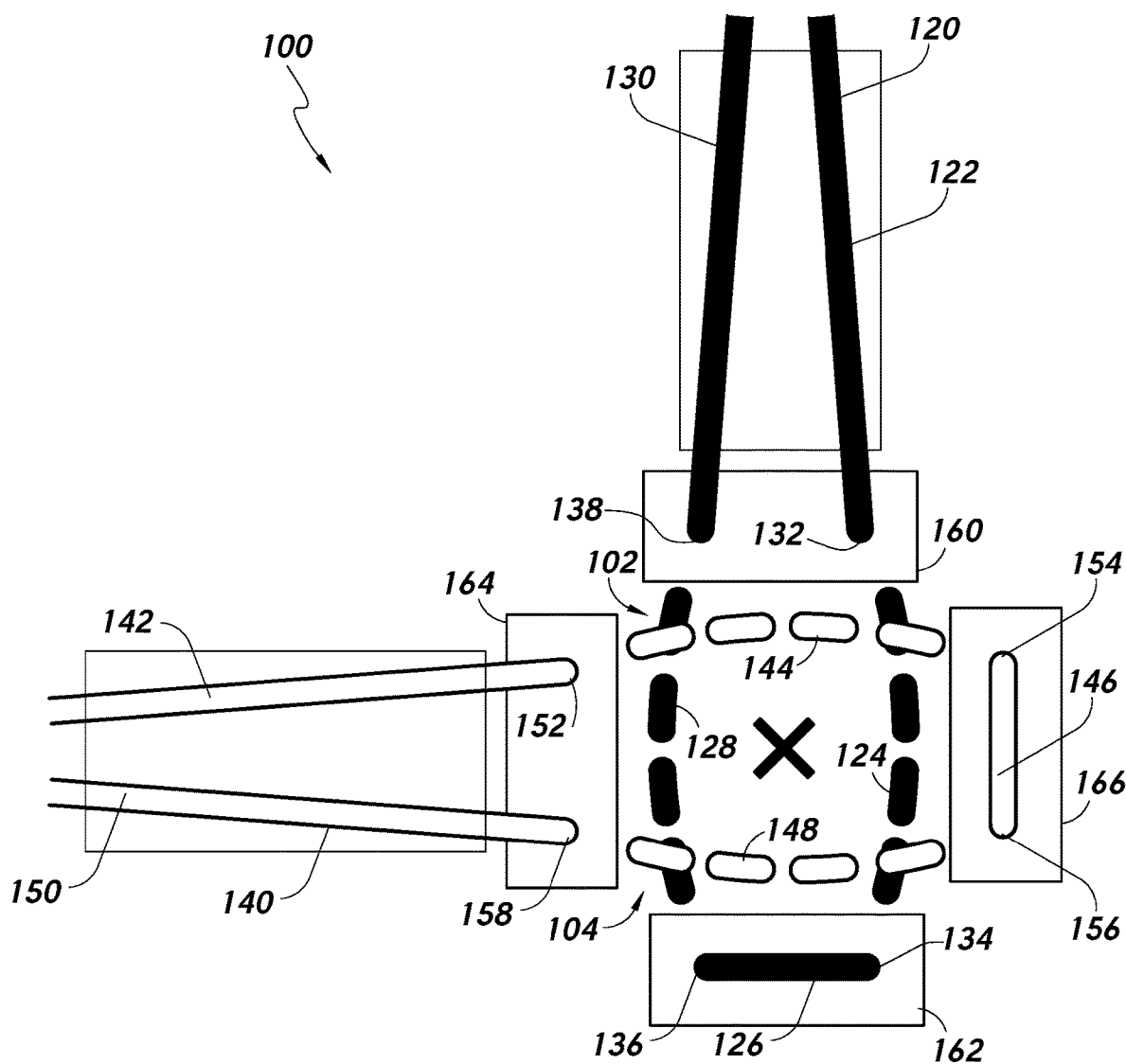
FIG. 4 is a plan view of an example of a traditional purse-string suture structure.

An example of a traditional purse-string suture structure 100 is shown schematically in FIG. 4. The traditional purse-string structure 100 can comprise a first purse-string suture 102 and a second purse-string suture 104. FIG. 4 shows the first purse-string suture 102 and the second purse-string suture 104 arranged around an opening in a target tissue. The opening is marked by "X" in FIG. 4. The first purse-string suture 102 can be coupled to a first pad 160 and a second pad 162. The second purse-string suture 104 can be coupled to a third pad 164 and a fourth pad 166. The first purse-string suture 102 and the second purse-string suture 104 can be arranged in a crisscross pattern. In some instances, the first purse-string suture 102 and the second purse-string suture 104 can be perpendicular or substantially perpendicular to one another. In some instances, the first pad 160 and the second pad 162 can be arranged in opposing fashion around the opening, and the third pad 164 and the fourth pad 166 can be arranged in opposing fashion around the opening. The first and second pads 160, 162 can be perpendicular or substantially perpendicular to the third and fourth pads 164, 166.

Referring to FIG. 4, the first purse-string suture 102 can be configured to be stitched using a first suture 120. The first suture 120 can comprise a first distal portion 122 coupled to the first pad 160, a first portion 124 configured to be stitched through the target tissue and extend between the first pad 160 and the second pad 162, a portion 126 configured to be positioned over the second pad 162, a second portion 128 configured to be stitched through the target tissue and extend between the second pad 162 to the first pad 160, and a second distal portion 130 coupled to the first pad 160. A distal end 132 of the first distal portion 122 can be positioned at a first location on the first pad 160. First and second distal ends 134, 136 of the portion 126 can be positioned at a first and second location on the second pad 162, respectively. A distal end 138 of the second distal portion 130 can be positioned at a second location on the first pad 160. The first portion 124 of the first suture 120 can extend alongside the fourth pad 166 and the second portion 128 of the first suture 120 can extend alongside the third pad 164.

The second purse-string suture 104 can be configured to be stitched using a second suture 140. The second suture 140 can comprise a first distal portion 142 coupled to the third pad 164, a first portion 144 configured to be stitched through the target tissue and extend between the third pad 164 and the fourth pad 164, a portion 146 configured to be positioned over the fourth pad 166, a second portion 148 configured to be stitched through the target tissue and extend between the fourth pad 166 to the third pad 164, and a second distal portion 150 coupled to the third pad 164. A distal end 152 of the first distal portion 142 can be positioned at a first location on the third pad 164. First and second distal ends 154, 156 of the portion 146 can be positioned at a first and second location on the fourth pad 166, respectively. A distal end 158 of the second distal portion 150 can be positioned at a second location on the third pad 164. The first portion 144 of the second suture 140 can extend alongside the first pad 160 and the second portion 148 of the second suture 140 can extend alongside the second pad 162 such that the first purse-string suture 102 and the second purse-string suture 104 can be arranged in a crisscross pattern.

The opening shown in FIG. 4 can be formed on the heart wall, such as for performing a mitral valve repair procedure. One or more tethers coupled to a mitral valve leaflet can extend through the opening. The purse-string suture structure 100 as described with reference to FIG. 4 can cause damage to the one or more tethers, which can lead to breakage of the tethers. Tensioning of purse-string sutures 102, 104 can cause undesired folding of the tissue proximate and/or adjacent to the opening, which can in turn result in concentrated loading on portions of the tethers. The pattern of stitching, such as the crisscross pattern, of the purse-string sutures 102, 104 can result in contact between the sutures and the one or more tethers, thereby contributing to damage and breakage of the tethers.

The disclosure herein provides one or more devices and methods related to improved purse-string sutures which can advantageously provide desired closure of an opening in a tissue while reducing or preventing damage to any tethers extending through the opening. One or more purse-string sutures described herein can facilitate desired closure of the openings so as to provide hemostasis while reducing or avoiding loading upon and/or abrasion of the tethers. The purse-string sutures described herein can maintain sufficient clearance around the tethers to reduce or eliminate contact between the sutures and the tethers. The purse-string sutures described herein can be used in various applications, including in heart surgeries as described herein. In some instances, the purse-string sutures can be used in beating-heart surgeries. In some instances, the purse-string sutures described herein can be used in heart valve surgeries, including in mitral valve repair surgeries, such as beating-heart mitral valve repair surgeries. In some instances, the purse-string sutures can be used to suture openings formed to perform beating-heart surgeries for deploying one or more tethers a mitral valve leaflet. The purse-string sutures can be used to reduce and/or seal openings formed in apex regions of heart walls. The purse-string sutures described herein can provide safe zones through which one or more tethers can be extended such that the tethers can avoid undesired damage.

A purse-string suture structure can comprise one or more purse-string sutures coupled to a plurality of pads. Respective sutures can be coupled to each of the plurality of pads to provide the one or more purse-string suture structures. Corresponding portions of each the one or more sutures, such as a suture stitch, can be positioned over an upper surface of each of the pads to raise the corresponding portions of each suture above the surface of the target tissue. As described herein, the purse-string suture structures can be formed in the heart wall. The plurality of pads can be positioned over the pericardium, including directly on and in contact with the pericardium. Raising portions of the sutures above the target tissue over a plurality of pads can facilitate providing respective safe zones beneath the pads through which tethers can extend without or substantially without the tethers becoming damaged. For example, raising portions of the sutures above the pericardium over the plurality of pads can provide corresponding safe zones which extend beneath the plurality of pads into the heart wall. A safe zone can comprise a volume beneath at least a portion of a corresponding pad. The safe zones under the pads can be maintained after the purse-string suture is tensioned, including to close the opening around any instrumentation and/or seal the opening. In some instances, the safe zones can comprise an orientation aligned with the path of one or more tethers coupled to a heart valve leaflet, such as a mitral valve leaflet. Inclusion of the pads around the opening can reduce or prevent abrasion of the tethers. The pads can provide corresponding safe zones through which one or more tethers can pass without or substantially without undesired damage. In some instances, the number of safe zones corresponds to the number of pads. In some instances, a purse-string suture structure can comprise two pads. In some instances, three pads can be included. In some instances, four pads can be included. For example, a purse-string suture structure comprising two pads, three pads and four pads can provide two safe zones, three safe zones and four safe zones, respectively. In some instances, the plurality of pads can be evenly distributed around the opening. The number and/or arrangement of pads around the opening can be selected based on a variety of factors, including for example, a size of the opening, a size of the pads, paths of the tethers and/or a number of tethers.

In some instances, a purse-string suture structure can comprise a plurality of purse-string sutures formed in a concentric pattern on a target tissue. More purse-string sutures can be formed around an opening to provide increased suture strength. In some instances, a purse-string suture structure can comprise a plurality of purse-string sutures each coupled to a plurality of pads. For example, a purse-string suture structure can comprise two concentric purse-string sutures configured to be positioned around a tissue opening, and a plurality of pads coupled to both of the purse-string sutures. The plurality of pads can be configured to be positioned at predetermined positions around the tissue opening. In some instances, the predetermined positions of the plurality of pads can be selected based on the paths of the tethers. In some instances, the concentric pattern can facilitate providing the safe zones as described herein. In some instances, forming a concentric pattern can facilitate providing desired clearance around the one or more tethers. Maintaining clearance between the one or more tethers and the purse-string sutures can prevent or eliminate damage to the tethers extending through the tissue opening.

In some instances, a method of forming a purse-string suture structure can comprise forming a first purse-string suture along a first path around an opening using a first suture and a second purse-string suture along a second path around and concentric with the first path using a second suture. A plurality of pads can be coupled to the first and second sutures. For example, three pads can be coupled to the first and second sutures such that corresponding portions of the first suture and second suture can be positioned over an upper surface of each of the three pads. The upper surface can be configured to be oriented away from the target tissue, while a lower surface can be configured to be oriented toward the target tissue. In some instances, the pads can be positioned on and in contact with the target tissue. The length of suture positioned over an upper surface of a pad can be selected to raise a desired portion of the suture over the pad so as to facilitate providing a desired safe zone, while allowing desired securing of the pad to the target tissue. In some instances, positions of distal ends of the length of suture positioned over a pad can be selected to prevent or reduce edges of the pad from flipping upward and more central portions of the pad from caving downward, including when the purse-string suture is tightened. Warping of the pads can induce irritation, inflammation and/or scarring in the target tissue, such as in the pericardium. In some instances, the distal ends can be up to about 2 millimeters (mm) from a nearest edge of the pad, including about 1 mm to about 2 mm from the nearest edge.

Although purse-string suture structures described herein primarily include two concentric purse-string sutures, purse-string suture structures can include more or fewer purse-string sutures. In some instances, a purse-string suture structure can comprise a single purse-string suture arranged around an opening in a target tissue. In some instances, a purse-string suture structure can comprise more than two purse-string sutures concentrically arranged around the opening in the target tissue. In some instances, a purse-string suture structure can comprise three purse-string sutures concentrically arranged around the opening. In some instances, a purse-string suture structure can comprise four purse-string sutures concentrically arranged around the opening. In some instances, a purse-string suture structure can comprise five purse-string sutures concentrically arranged around the opening. More purse-string sutures can be used to provide added strength for the purse-string suture structure.

As used herein, a "pad" can refer to any number of padding material configured to provide space between a suture portion and the target tissue. In some instances, a pad can be a pledget. The pads as described herein can have a number of different shapes. In some instances, one or more of the pads can have a rectangular shape comprising two opposing longer edges and two opposing shorter edges. The purse-string sutures can described herein can be formed using sutures made of a variety of materials. In some instances, one or more of the purse-string sutures can be stitched using a suture comprising polypropylene (e.g., Prolene® polypropylene sutures, including Ethicon® 3-0 Prolene® sutures).

The methods, operations, steps, etc. described herein can be performed on a living animal or on a non-living cadaver, cadaver heart, simulator (e.g. with the body parts, tissue, etc. being simulated), etc.

Figure 5:
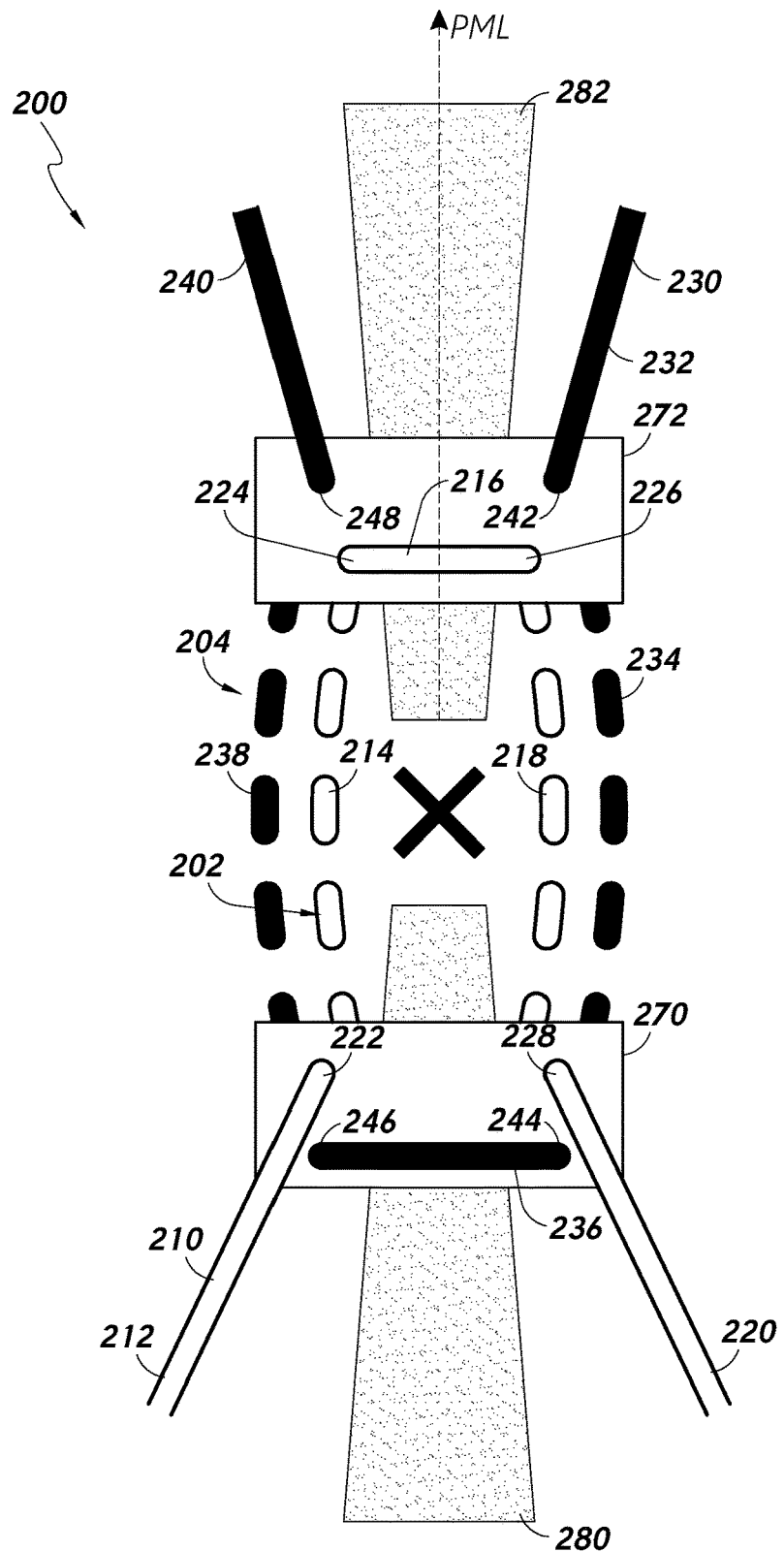
FIG. 5 is a plan view of an example of a purse-string suture structure, according to some instances, where the structure comprises two concentric purse-string sutures positioned around a target tissue opening and where two pads are coupled to the each of the sutures, according to some instances.

FIG. 5 is a schematic plan view of an example of a purse-string suture structure 200 comprising a first purse-string suture 202 and a second purse-string suture 204 positioned around an opening in a target tissue and both coupled to a first pad 270 and a second pad 272. The first purse-string suture 202 can be formed along a first path around the opening and the second purse-string suture 204 can be formed around the opening along a second path. The first pad 270 and the second pad 272 can be positioned at a first position and a second position, respectively, along the first path and the second path. The second path can surround and be concentric with the first path such that the second purse-string suture 204 surrounds and is concentric with the first purse-string suture 202. The opening in the target tissue is marked by the "X" shown in FIG. 5. The purse-string suture structure 200 can have one or more of a circular, oval and rectangular shape. For example, the purse-string suture structure 200 can have one or more of a concentric circular, oval and rectangular shape. In some instances, the first purse-string suture 202 and the second purse-string suture 204 can both have an oval or substantially oval shape. In some instances, the first purse-string suture 202 and the second purse-string suture 204 can both have a circular or substantially circular shape.

A first suture 210 can be configured to form the first purse-string suture 202. A second suture 230 can be configured to form the second purse-string suture 204. The first suture 210 can be used to stitch along the first path around the target opening. The second suture 230 can be used to stitch along the second path around the target opening. In some instances, the target opening can be on a heart wall. The target opening can be formed in the heart wall to obtain transapical access to a mitral valve leaflet, such as to perform a mitral valve repair procedure. As described herein, the opening can be formed in the apex region of the heart wall. One or more purse-string sutures as described herein can be used for suturing the openings formed in the heart wall. The first suture 210 and/or the second suture 230 can be threaded through the pericardium and one or more layers of the heart wall. In some instances, the first suture 210 and the second suture 230 can be threaded through at least a portion of the myocardium, for example to provide sufficient depth into the target tissue to hold the respective purse-string sutures. In some instances, the first suture 210 and the second suture 230 can be threaded through each of the pericardium, the epicardium and at least a portion of the myocardium. The first pad 270 and the second pad 272 can be positioned over the pericardium of the heart wall. For example, the first pad 270 and the second pad 272 can be positioned directly on and in contact with the pericardium, where a lower surface of each of the pads 270, 272 can be oriented towards the pericardium and an upper surface of each of the pads 270, 272 can be oriented in an opposing direction away from the pericardium.

The first pad 270 and the second pad 272 can be at respective positions around the target opening. In some instances, the positions of one or more of the pads 270, 272 can be predetermined based at least in part on a number of tethers and/or paths of the tethers. In some instances, the positions of the pads 270, 272 can be selected to facilitate providing desired orientations for the safe zones and/or number of safe zones. In some instances, the first pad 270 and the second pad 272 can be evenly distributed around the target opening. For example, the first pad 270 and the second pad 272 can be positioned around the target opening along the first path and the second path at opposing or substantially opposing positions. One or both of the first pad 270 or the second pad 272 can be aligned with a direction of a posterior mitral valve leaflet (PML). The direction of the posterior mitral valve leaflet (PML) can comprise a path extending between the opening in the target tissue and the posterior mitral valve leaflet. For example, as described in further detail herein, the posterior mitral valve leaflet (PML) direction can comprise a path on an exterior of a heart, such as on a pericardium, where the path extends between the tissue opening and the posterior mitral valve leaflet (PML). As shown in FIG. 5, in some instances, both the first pad 270 and the second pad 272 can be aligned with the direction of the posterior mitral valve leaflet (PML). For example, the first pad 270 and the second pad 272 can be at opposing positions relative to one another around the target opening such that both the first pad 270 and the second pad 272 can be aligned with the direction of the posterior mitral valve leaflet (PML). In some instances, the first pad 270 and the second pad 272 may not be positioned at opposing positions around the target opening.

The first suture 210 and the second suture 230 can be stitched in the target tissue around the opening and coupled to each of the pads. For example, each of the sutures can be stitched to the pads such that corresponding suture stitches can be positioned over the pads. Referring again to FIG. 5, the first suture 210 can comprise a first distal portion 212. The first distal portion 212 can be coupled to the first pad 270. The first pad 270 can be at a first position along the first path and the second path. The first suture 210 can comprise a first tissue portion 214 configured to be stitched through the target tissue and extend between the first pad 270 and the second pad 270 along the first path. The first suture 210 can be coupled to the second pad 272, the first suture 210 comprising a second pad portion 216, such as a suture stitch, configured to be positioned over the second pad 272, such as on and in contact with the second pad 272. The second pad 272 can be at a second position along the first path and the second path. A second tissue portion 218 of the first suture 210 can be configured to be stitched through the target tissue and extend between the second pad 272 and the first pad 270 along the first path. A second distal portion 220 of the first suture 210 can be coupled to the first pad 270, such that the first suture 210 can surround the target opening.

The second suture 230 can comprise a first distal portion 232. The first distal portion 232 can be coupled to the second pad 272. The second suture 230 can comprise a first tissue portion 234 configured to be stitched through the target tissue and extend between the second pad 272 and the first pad 270 along the second path. The second suture 230 can be coupled to the first pad 270, the second suture 230 comprising a first pad portion 236, such as a suture stitch, configured to be positioned over the first pad 270, such as on and in contact with the first pad 270. A second tissue portion 238 of the second suture 230 can be configured to be stitched through the target tissue and extend between the second pad 272 and the first pad 270 along the second path. A second distal portion 240 of the second suture 230 can be coupled to the second pad 272, such that the second suture 230 can surround the target opening. The second suture 230 can be tensioned to form the second purse-string suture 204 around the target opening. The first suture 210 can be tensioned to form the first purse-string suture 202 around the target opening. For example, the first suture 210, including the first distal portion 212 and the second distal portion 220 of the first suture 210, can be tensioned to form the first purse-string suture 202. The second suture 230, including the first distal portion 232 and the second distal portion 240 of the second suture 230, can be tensioned to form the second purse-string suture 204. The first purse-string suture 202 and the second purse-string suture 204 can be formed around the target opening, such as to close the target opening around a medical instrument and/or a valve leaflet tether, and/or to seal the target opening.

A method of forming the first purse-string suture 202 can comprise coupling the second pad 272 to the first suture 210. The second pad 272 can be stitched to the first suture 210 such that the second pad portion 216 can be positioned over the upper surface of the second pad 272. For example, the first suture 210 can be threaded through the second pad 272 from the lower surface of the second pad 272 through to the upper surface of the second pad 272. The first suture 210 can then be extended along the upper surface of the second pad 272 to position the second pad portion 216 over the upper surface. Alternatively, the first suture 210 can be threaded through from the upper surface through to the lower surface of the second pad 272 at predetermined locations on the second pad 272 to position the second pad portion 216 over the upper surface. The second pad 272 can be positioned at the second position over the target tissue. The first suture 210 can be stitched through the target tissue and extended from each of the two respective predetermined locations on the second pad 272, such as locations proximate and/or adjacent to opposing sides of the second pad 272, along the first path toward the first position such that the first tissue portion 214 and the second tissue portion 218 can be formed. The first suture 210 can subsequently be coupled to the first pad 270. The first distal portion 212 and the second distal portion 220 of the first suture 210 can be threaded through the first pad 270 from the lower surface of the first pad 270 through to the upper surface of the first pad 270. The first pad 270 can then be positioned at its position along the first path and second path.

A method of forming the second purse-string suture 204 can comprise coupling the second suture 230 to the first pad 270. The second suture 230 can be stitched to the first pad 270 such that the second suture 230 can comprise the first pad portion 236 positioned over the upper surface of the first pad 270. For example, the second suture 230 can be threaded through the first pad 270 from the lower surface through to the upper surface of the first pad 270 and extended along the upper surface of the first pad 270 to position the first pad portion 236 over the upper surface. Alternatively, the second suture 230 can be threaded through from the upper surface through to the lower surface of the first pad 270 at predetermined locations on the first pad 270 to position the first pad portion 236 over the upper surface. The second suture 230 can be stitched through the target tissue and extended from the respective predetermined locations on the first pad 270, such as locations proximate and/or adjacent to each of two opposing sides of the first pad 270, along the second path toward the second position such that the first tissue portion 234 and the second tissue portion 238 can be formed. The second suture 230 can then be coupled to the second pad 272, for example comprising threading the first distal portion 232 and the second distal portion 240 of the second suture 230 through the second pad 272 from the lower surface through to the upper surface of the second pad 272.

A suture can be coupled to a plurality of pads in a number of different sequences. In some instances, the first suture 210 can be coupled to the first pad 270 prior to being coupled to the second pad 272. In some instances, the first suture 210 can be threaded through the first pad 270 such that the first distal portion 212 can be coupled to the first pad 270. The first suture 210 can be stitched through the target tissue along the first path from the first position to the second position so as to form the first tissue portion 214. The first suture 210 can then be coupled to the second pad 272 to position the second pad portion 216 over the second pad 272. The first suture 210 can be subsequently stitched through the target tissue along the first path from the second position to the first position so as to form the second tissue portion 218. The second distal portion 220 can then be coupled to the first pad 270. In some instances, the second distal portion 220 can be coupled to the first pad 270 prior to coupling the first distal portion 212 to the first pad 270. In some instances, the second tissue portion 218 can be formed prior to forming the first tissue portion 214.

In some instances, the second suture 230 can be coupled to the second pad 272 prior to being coupled to the first pad 270. For example, the first distal portion 232 can be coupled to the second pad 270, and the second suture 230 can then be stitched through the target tissue along the second path from the second position to the first position so as to form the first tissue portion 234. The second suture 230 can be coupled to the first pad 270 and the first pad portion 236 can be positioned over the first pad 270. The second suture 230 can be stitched through the target tissue along the second path from the first position to the second position so as to form the second tissue portion 238. The second distal portion 240 can then be coupled to the second pad 272. In some instances, the second distal portion 240 can be coupled to the second pad 272 prior to coupling the first distal portion 232 to the second pad 272. In some instances, the second tissue portion 238 can be formed prior to forming the first tissue portion 234.

In some instances, a length of the corresponding portions of the first suture 210 and second suture 230 configured to be positioned over the second pad 272 and the first pad 270, respectively, can be predetermined to reduce or avoid irritation of the target tissue. For example, locations of the distal ends 224, 226 of the second pad portion 216 on the second pad 272 and/or the distal ends 244, 246 of the first pad portion 236 on the first pad 270 can be selected to reduce or eliminate warping of the respective pad, including bending upward of the edges of the pad. In some instances, a length of the first pad portion 236 and/or second pad portion 216 can be selected to provide a desired size for the safe zones.

In some instances, a length of the first pad portion 236 and second pad portion 216 can be selected to reduce or avoid tissue irritation, and/or provide desired safe zones, while ensuring a secure attachment of the pads to the sutures. In some instances, distal ends of a portion of the first suture 210 and/or second suture 230 configured to be positioned over the first pad 270 and/or second pad 272 can be less than about 2 millimeters (mm) from respective nearest edge(s) of the pad, including about 1 mm to about 2 mm from the respective nearest edge(s). Referring to FIG. 5, in some instances, the first pad portion 236 can comprise distal ends 244, 246 at less than about 2 millimeters (mm) from respective nearest edge(s) of the first pad 270, including about 1 mm to about 2 mm from the respective nearest edge(s). In some instances, the second pad portion 216 of the first suture 210 can comprise distal ends 224, 226 at less than about 2 millimeters (mm) from respective nearest edge(s) of the second pad 272, including about 1 mm to about 2 mm from the respective nearest edge(s). The first pad portion 236 and the second pad portion 216 can extend along paths which are less than about 2 millimeters (mm) from the nearest edge of the respective pad, including about 1 mm to about 2 mm from the nearest edge. In some instances, ends 222, 228 of the first distal portion 212 and second distal portion 220 of the first suture 210, and/or the ends 242, 248 of the first distal portion 232 and/or second distal portion 240 of the second suture 230 can be positioned less than about 2 millimeters (mm) from the respective nearest edge(s) of the corresponding pad, including about 1 mm to about 2 mm from the respective nearest edge(s). In some instances, a length of a suture portion can be the same as or similar to a distance between distal ends of distal portions coupled to the same pad.

In some instances, the first pad 270 and the second pad 272 can each have a rectangular shape. For example, a longer edge of the rectangle can be oriented toward the opening in the target tissue, while an opposing longer edge can be oriented away from the opening. Shorter edges of the rectangle can extend between the longer edges. In some instances, the first pad portion 236 can extend along a path less than about 2 millimeters (mm) from a nearest longer edge of the first pad 270, such as the longer edge oriented farther away from the opening. The distal ends 244, 246 of the first pad portion 236 can be less than about 2 millimeters (mm) from respective nearest shorter edges of the first pad 270. In some instances, the second pad portion 216 can extend along a path less than about 2 millimeters (mm) from a nearest longer edge of the second pad 272, such as the longer edge oriented closer to the opening. The distal ends 224, 226 of the second pad portion 216 can be less than about 2 millimeters (mm) from respective nearest shorter edges of the second pad 272. Ends 222, 228 of the distal portions 212, 220 of the first suture 210 can be less than about 2 millimeters (mm) from one or both of the nearest longer edge (e.g., the longer edge closer to the opening) and shorter edge. Ends 242, 248 of the distal portions 232, 240 of the second suture 230 can be positioned less than about 2 millimeters (mm) from one or both of the nearest longer edge (e.g., the longer edge farther from the opening) and shorter edge. In some instances, a pad can have a rounded shape, for example comprising an arcuate edge, such that an end of a suture portion is positioned less than about 2 millimeters (mm) from one nearest edge.

FIG. 5 shows the respective distal portions of the first suture 210 and second suture 230 as being coupled to different pads. The distal portions of the first suture 210 is shown as being coupled to the first pad 270 and the distal portions of the second suture 230 is shown as being coupled to the second pad 272. In some instances, the distal portions of both of the first suture 210 and the second suture 230 can be coupled to the same pad, such as both being coupled to the first pad 270 or both being coupled to the second pad 272.

Referring again to FIG. 5, a first safe zone 280 can extend under the first pad 270 and a second safe zone 282 can extend under the second pad 272. The safe zones 280, 282 can extend downward into the target tissue (into the page). One or more tethers can extend through each of the safe zones 280, 282 without or substantially without being damaged. For example, a tether can extend from a mitral valve leaflet, such as a posterior mitral valve leaflet, and through a safe zone such that a distal end of the tether can be extended through the opening to couple to an exterior of the heart wall. The purse-string sutures 202, 204 can be closed around the tether such that the tether is not or substantially not damaged. For example, tensioning of the purse-string sutures 202, 204 can result in closure of the opening around one or more tethers extending through the opening without or substantially without damaging the one or more tethers.

A height of each of the safe zones 280, 282 can be a distance into the target tissue which the respective safe zone extends. For example, the safe zones 280, 282 can have a height equal or similar to a thickness of the heart wall beneath the respective pad. The safe zones 280, 282 can have a width similar or equal to a length of a suture portion positioned over a pad. For example, a width of a safe zone can be similar or equal to a length of a corresponding portion of suture raised above the target tissue over a pad. In some instances, the first safe zone 280 can have a width similar or equal to a length of the first pad portion 236 and/or a distance between the ends 222, 228 of the distal portions 212, 220. In some instances, the first safe zone 280 can have a width similar or equal to a shorter one of the length of the first pad portion 236 and the distance between the ends 222, 228. In some instances, the second safe zone 282 can have a width similar or equal to a length of the second pad portion 216 and/or a distance between the ends 242, 248 of the distal portion 232, 240 of the second suture 230. In some instances, the second safe zone 282 can have a width similar or equal to a shorter one of the length of the first pad portion 216 and the distance between the ends 242, 248. A length of each of the safe zones 280, 282 can be a dimension perpendicular or substantially perpendicular to both the height and width of the respective safe zone. For example, the safe zones 280, 282 can extend across an entire width of each of the first pad 270 and second pad 272, respectively. Each of the safe zones 280, 282 can have a length longer than a dimension extending between opposing longer edges of a corresponding rectangular pad as described herein. For example, the safe zones 280, 282 can have a length longer than a width of the corresponding pad. In some instances, the safe zones 280, 282 can extend from the opening in the target tissue to at least an outer edge of the purse-string suture structure 200.

Figure 6A:
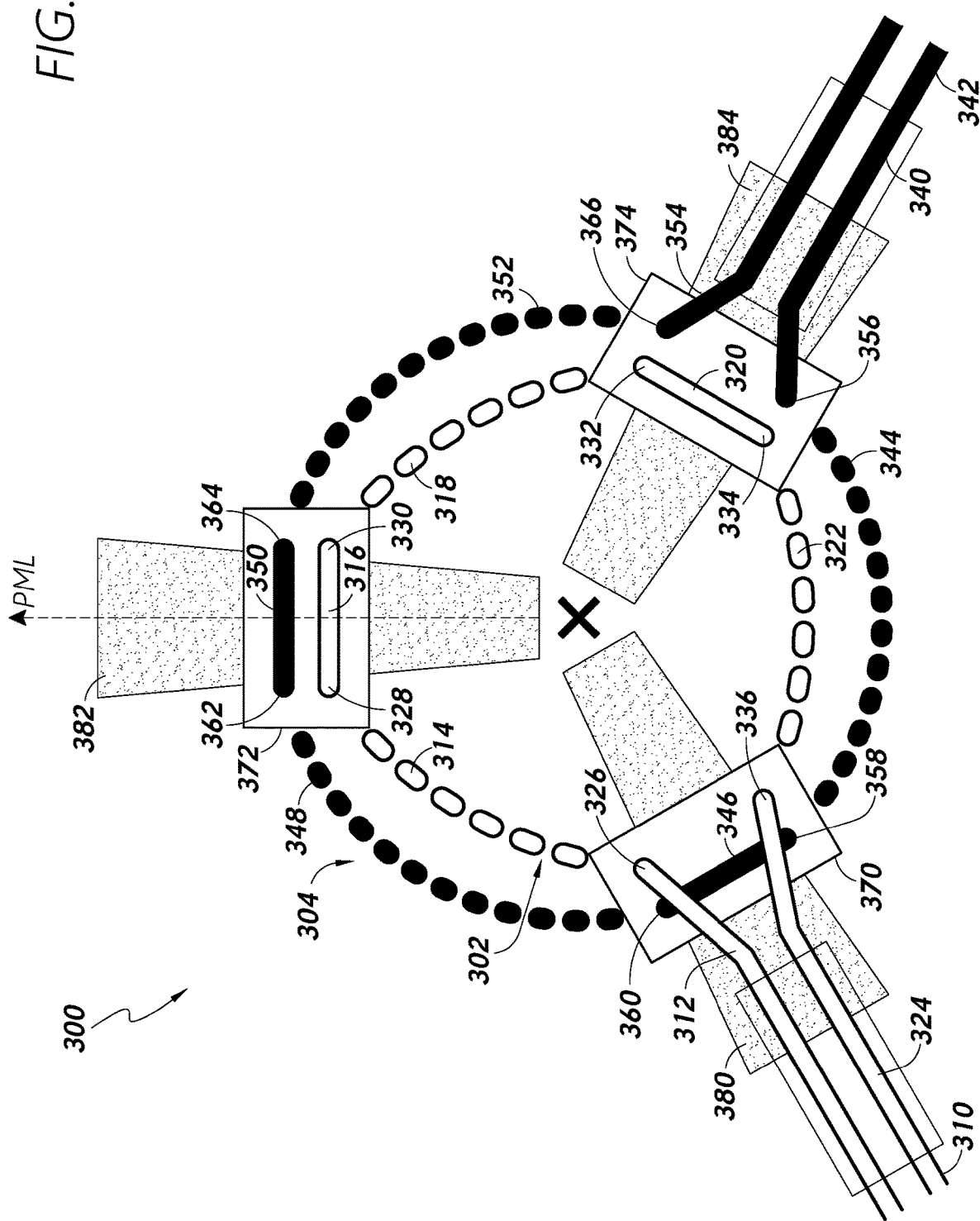
FIGS. 6A and 6B are plan views of examples of purse-string suture structures, according to some instances, each structure comprising two concentric purse-string sutures positioned around a respective target tissue opening, where each of the sutures are coupled to three pads, according to some instances.
Figure 6B:
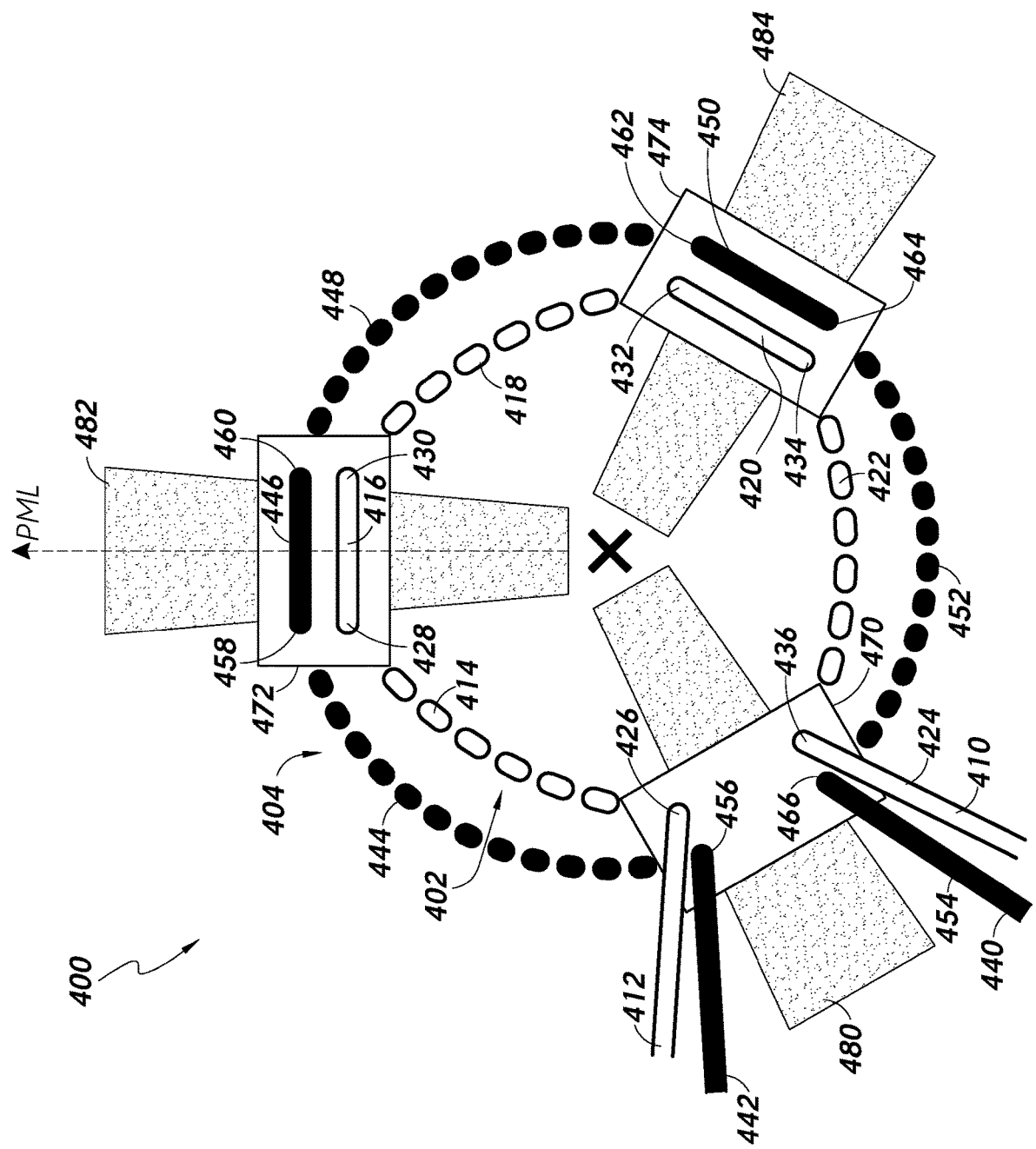

In some instances, a purse-string suture can be coupled to three pads. FIGS. 6A and 6B are schematic plan views of examples of purse-string suture structures 300, 400, respectively. Each purse-string suture structure 300, 400 can comprise a first purse-string suture 302, 402 and a second purse-string suture 304, 404 positioned around a respective opening in a target tissue. Both sutures in each of the structures 300, 400 are coupled to a respective first pad 370, 470, second pad 372, 472 and third pad 374, 474. The respective openings are marked by "X" in FIGS. 6A and 6B.

Distal portions of the first purse-string suture 302 and the second purse-string suture 304 of the purse-string suture structure 300 shown in FIG. 6A can be coupled to different ones of the three pads. In FIG. 6B, distal portions of the first purse-string suture 402 and the second purse-string suture 404 of the purse-string suture structure 400 can be coupled to the same one of the three pads. The distal portions of the sutures can be arranged in a number of different manners relative to the three pads. A selection can be made based on convenience and/or preference of an operator.

Referring to FIGS. 6A and 6B, the second purse-string sutures 304, 404 can surround and be concentric with the first purse-string sutures 302, 402. The first purse-string sutures 302, 402 and/or the second purse-string sutures 304, 404 can have one or more of a circular, oval and hexagonal shape. In some instances, each of the first purse-string sutures 302, 402 and the second purse-string sutures 304, 404 can have a circular or substantially circular shape. In some instances, each of the first purse-string sutures 302, 402 and the second purse-string sutures 304, 404 can have a hexagonal or substantially hexagonal shape. The purse-string suture structures 300, 400 can be positioned in the heart wall for reducing a size and/or sealing of an opening formed in the heart wall, such as that described with reference with FIG. 5. For example, the sutures of the purse-string suture structures 300, 400 can be threaded through the pericardium and one or more layers of the heart wall, including through at least a portion of the myocardium. In some instances, the first pads 370, 470, second pads 372, 472 and third pads 374, 474 can be placed over the pericardium, including directly on and in contact with the pericardium. A lower surface of each of the pads 370, 372, 374, 470, 472, 474 can be oriented towards the pericardium and an upper surface of each of the pads 370, 372, 374, 470, 472, 474 can be oriented in an opposing direction away from the pericardium. A first suture 310, 410 can be used to stitch the first purse-string sutures 302, 402 along a respective first path and a second suture 340, 440 can be used to stitch the second purse-string sutures 304, 404 along a respective second path.

Each of the first pads 370, 470, second pads 372, 472 and third pads 374, 474 can be at a corresponding first position, a second position and a third position around the target opening along the respective first path and second path. Positions of one or more of the pads can be predetermined based at least in part on a number of tethers and/or paths of the tethers, such as to facilitate providing desired orientations of the safe zones and/or number of safe zones for the tethers. In some instances, the first pads 370, 470, second pads 372, 472 and third pads 374, 474 can be evenly distributed around the target opening. For example, the pads 370, 372, 374, 470, 472, 474 can be positioned equidistant from one another around the target opening along the first path and the second path. In some instances, the pads 370, 372, 374, 470, 472, 474 may not be evenly distributed around the target opening. One or more of the pads can be aligned with a direction of a posterior mitral valve leaflet (PML). In some instances, a pad not coupled to any distal portions of a suture can be aligned with the direction of the posterior mitral valve leaflet (PML). FIGS. 6A and 6B show the second pad 372 being aligned with the direction of the posterior mitral valve leaflet (PML). Referring to FIG. 6B, in some instances, the third pad 474 can be aligned with the direction of the posterior mitral valve leaflet (PML).

Referring to FIG. 6A, the first suture 310 can comprise: a first distal portion 312 coupled to the first pad 370, a first tissue portion 314 stitched through the target tissue and extending between the first pad 370 and the second pad 372 along the first path, a second pad portion 316 positioned over the second pad 372, including on and in contact with the second pad 372, a second tissue portion 318 stitched through the target tissue and extending between the second pad 372 and the third pad 374 along the first path, a third pad portion 320 configured to be positioned over the third pad 374, including on and in contact with the third pad 374, a third tissue portion 322 stitched through the target tissue and extending between the third pad 374 and the first pad 370, and a second distal portion 324 coupled to the first pad 370. The second suture 340 can comprise: a first distal portion 342 coupled to the third pad 374, a first tissue portion 344 stitched through the target tissue and extending between the third pad 374 and the first pad 370 along the second path, a first pad portion 346 positioned over the first pad 370, including on and in contact with the first pad 370, a second tissue portion 348 stitched through the target tissue and extending between the first pad 370 and the second pad 372 along the second path, a second pad portion 350 positioned over the second pad 372, including on and in contact with the second pad 372, a third tissue portion 352 stitched through the target tissue and extending between the second pad 372 and the third pad 374, and a second distal portion 354 coupled to the third pad 374. In some instances, the second pad portion 350 of the second suture 340 can be parallel or substantially parallel to the second pad portion 316 of the first suture 310.

The first suture 310 and second suture 340 can be tensioned to form the first purse-string suture 302 and the second purse-string suture 304, respectively, around the target opening. For example, the first suture 310 and second suture 340 can be tensioned to close the target opening around a medical instrument and/or valve leaflet tether, and/or to seal the target opening.

Referring to FIG. 6B, the purse-string suture structure 400 can have the first suture 410 and the second suture 440 arranged around the target opening such that the first distal portions 412, 442 and the second distal portions 424, 454 are coupled to the same pad, for example the first pad 470. Each of the first suture 410 and the second suture 440 can comprise: a respective first distal portion 412, 442 coupled to the first pad 470, a respective first tissue portion 414, 444 stitched through the target tissue and extending between the first pad 470 and the second pad 472 along the first path and second path, a respective second pad portion 416, 446 positioned over the second pad 472, including on and in contact with the second pad 472, a respective second tissue portion 418, 448 stitched through the target tissue and extending between the second pad 472 and the third pad 474 along the first path and second path, a respective third pad portion 420, 450 positioned over the third pad 474, including on and in contact with the third pad 474, a respective third tissue portion 422, 452 stitched through the target tissue and extending between the third pad 474 and the first pad 470 along the first path and second path, and a respective second distal portion 424, 454 coupled to the first pad 470. In some instances, the second pad portion 446 of the second suture 440 can be parallel or substantially parallel to the second pad portion 416 of the first suture 410. In some instances, the third pad portion 450 of the second suture 440 can be parallel or substantially parallel to the third pad portion 420 of the first suture 410.

In the purse-string suture structure 300 of FIG. 6A, the distal portions 312, 324 of the first suture 310 can be coupled to the first pad 370 while the distal portions 342, 354 of the second suture 340 can be coupled to the third pad 374.

Meanwhile, the purse-string suture structure 400 of FIG. 6B can have both the distal portions 412, 424 of the first suture 410 and both the distal portions 442, 454 of the second suture 440 coupled to the first pad 470. As described herein, the distal portions of the sutures can be arranged in a number of different manners relative to the three pads, and are not limited to the examples described with reference to FIGS. 6A and 6B.

Each of the pads can provide a corresponding safe zone. For example, in FIG. 6A, a first safe zone 380 can extend into the tissue under the first pad 370, a second safe zone 382 can extend into the tissue under the second pad 372 and a third safe zone 384 can extend into the tissue under the third pad 374. In FIG. 6B, a first safe zone 480 can extend into the tissue under the first pad 470, a second safe zone 482 can extend into the tissue under the second pad 472 and a third safe zone 484 can extend into the tissue under the third pad 474. A height of each of the safe zones 380, 382, 384, 480, 482, 484 can be a distance into the target tissue which the respective safe zone extends. For example, the safe zones 380, 382, 384, 480, 482, 484 can have a height equal or similar to a thickness of the heart wall beneath the respective pad. The safe zones 380, 382, 384, 480, 482, 484 can each have a width similar or equal to a length of a suture portion positioned over a corresponding pad and/or a distance between positions at which ends of suture distal portions are located on the corresponding pad. In some instances, one or more of the safe zones 380, 382, 384, 480, 482, 484 can each have a width which is the shorter of the length of a suture portion positioned over a corresponding pad and the distance between positions at which ends of suture distal portions are located on the corresponding pad. In some instances, one or more of the safe zones 380, 382, 384, 480, 482, 484 can each have a width which is the shorter of the lengths of suture portions positioned over a corresponding pad. Referring to FIG. 6A, the first safe zone 380 can have a width similar or equal to a shorter one of the length of the first pad portion 346 and the distance between the ends 326, 336. The second safe zone 382 can have a width similar or equal to a shorter one of the length of the second pad portions 316, 350. The third safe zone 384 can have a width similar or equal to a shorter one of the length of the third pad portion 320 and the distance between the ends 356, 366. Referring to FIG. 6B, the first safe zone 480 can have a width similar or equal to a shorter one of the distance between the ends 426, 436 and the distance between the ends 456, 466. The second safe zone 482 can have a width similar or equal to a shorter one of the length of the second pad portions 416, 446. The third safe zone 482 can have a width similar or equal to a shorter one of the length of the third pad portions 420, 450.

The safe zones 380, 382, 384, 480, 482, 484 can extend across an entire width of a respective pad. For example, each of the safe zones 380, 382, 384, 480, 482, 484 can have a length, such as a dimension perpendicular or substantially perpendicular to the width and height of the respective safe zone, longer than a width of the corresponding rectangular pad as described herein. In some instances, the safe zones 380, 382, 384, 480, 482, 484 can extend from the opening in the target tissue to at least an outer edge of the purse-string suture structures 300, 400.

In some instances, an orientation and/or length of the corresponding portions of the first sutures 310, 410 and second sutures 340, 440 configured to be positioned over the first pads 370, 470, the second pads 372, 472 and the third pads 374, 474 can be predetermined to reduce or avoid irritation of the target tissue, provide a desired size for the safe zones, while ensuring a secure attachment of the pads to the sutures. In some instances, positions of the ends of distal portions of the first sutures 310, 410 and second sutures 340, 440 on a respective pad, can be predetermined to reduce or avoid irritation of the target tissue, and/or provide a desired size for the safe zones, while ensuring a secure attachment of the pads to the sutures. Referring to FIG. 6A, the first pad portion 346 can comprise distal ends 358, 360 and/or the distal portions 312, 324 can comprise ends 326, 336 at less than about 2 millimeters (mm) from respective nearest edge(s) of the first pad 370, including about 1 mm to about 2 mm from the respective nearest edge(s). The second pad portion 316 of the first suture 310 can comprise distal ends 328, 330 and the second pad portion 350 of the second suture 340 can comprise distal ends 362, 364 at less than about 2 millimeters (mm) from respective nearest edge(s) of the second pad 372, including about 1 mm to about 2 mm from the respective nearest edge(s). The third pad portion 320 can comprise distal ends 332, 334 and/or the distal portions 342, 354 can comprise ends 356, 366 at less than about 2 millimeters (mm) from respective nearest edge(s) of the third pad 374, including about 1 mm to about 2 mm from the respective nearest edge(s). Referring to FIG. 6B, distal portions 412, 424 can comprise ends 426, 436 and/or the distal portions 442, 454 can comprise ends 456, 466 at less than about 2 millimeters (mm) from respective nearest edge(s) of the first pad 470, including about 1 mm to about 2 mm from the respective nearest edge(s). The second pad portion 416 of the first suture 410 can comprise distal ends 428, 430 and the second pad portion 446 of the second suture 440 can comprise distal ends 458, 460 at less than about 2 millimeters (mm) from respective nearest edge(s) of the second pad 472, including about 1 mm to about 2 mm from the respective nearest edge(s). The third pad portion 420 of the first suture 410 can comprise distal ends 432, 434 and the third pad portion 450 of the second suture 440 can comprise distal ends 462, 464 at less than about 2 millimeters (mm) from respective nearest edge(s) of the third pad 474, including about 1 mm to about 2 mm from the respective nearest edge(s). In some instances, corresponding suture portions positioned over pads can extend along a path less than about 2 millimeters (mm) from a nearest edge of the respective pad, including about 1 mm to about 2 mm from the nearest edge. For example, the first pad portion 346, second pad portions 316, 350, 416, 446 and third pad portions 320, 420, 450 can extend along paths which are less than about 2 millimeters (mm) from the nearest edge of the respective pad, including about 1 mm to about 2 mm from the nearest edge. In some instances, suture portions positioned over a same pad can have the same or similar length. In some instances, a length of a suture portion can be the same as or similar to a distance between distal ends of distal portions coupled to the same pad. In some instances, a distance between a first pair and a distance between a second pair of distal ends of distal portions coupled to the same pad can be the same or similar.

In some instances, the first pads 370, 470, the second pads 372, 472 and the third pads 374, 474 can each have a rectangular shape. For example, a longer edge of the rectangles can be oriented toward the opening in the target tissue, while an opposing longer edge can be oriented away from the opening. Shorter edges of the rectangles can extend between the longer edges. In some instances, corresponding portions of the first sutures 310, 410 positioned over the pads can extend along a path less than about 2 millimeters (mm) from respective longer edges which are closer to the opening in the target tissue. In some instances, corresponding portions of the second sutures 340, 440 positioned over the pads can extend along a path less than about 2 millimeters (mm) from respective longer edges which are farther away from the opening in the target tissue. In some instances, distal ends of the suture portions positioned over the pads can be at locations on the pad less than about 2 millimeters (mm) from a respective nearest shorter edge of the corresponding pad. Distal ends of the distal portions of the first sutures 310, 410 and second sutures 340, 440 can be less than about 2 millimeters (mm) from one or both of the nearest longer edge (e.g., one of the longer edge closer to the opening and the longer edge farther away from the opening) and the nearest shorter edge of the respective pad. In some instances, a pad can have a rounded shape, for example comprising an arcuate edge, such that an end of a suture portion is positioned less than about 2 millimeters (mm) from one nearest edge.

Methods of forming the purse-string structures 300, 400 of FIGS. 6A and 6B are described in further detail herein.

Figure 7A:
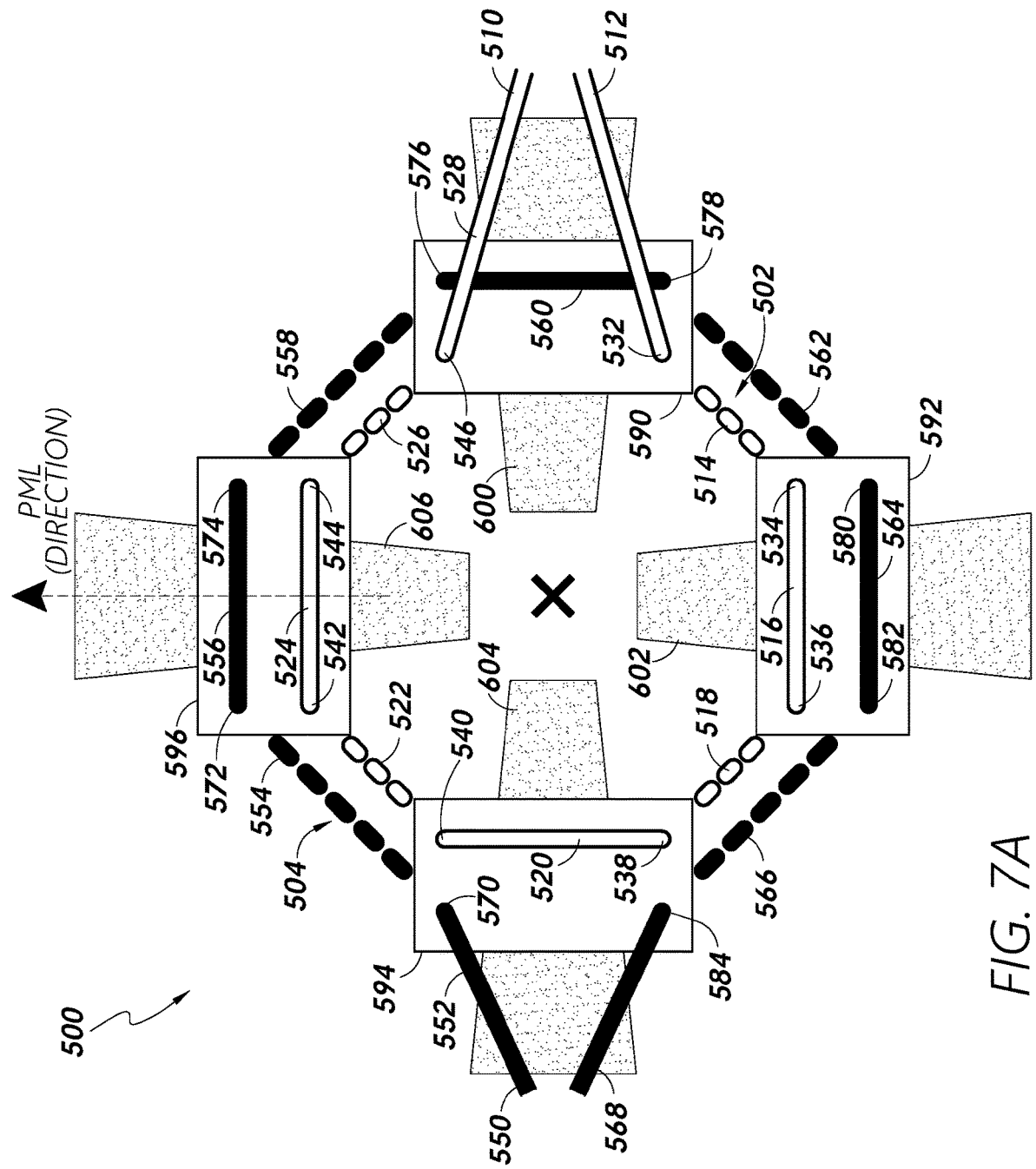
FIGS. 7A through 7C show an example of a purse-string suture structure comprising two concentric purse-string sutures positioned around a target tissue opening, and where both sutures are coupled to four pads, according to some instances.
Figure 7B:
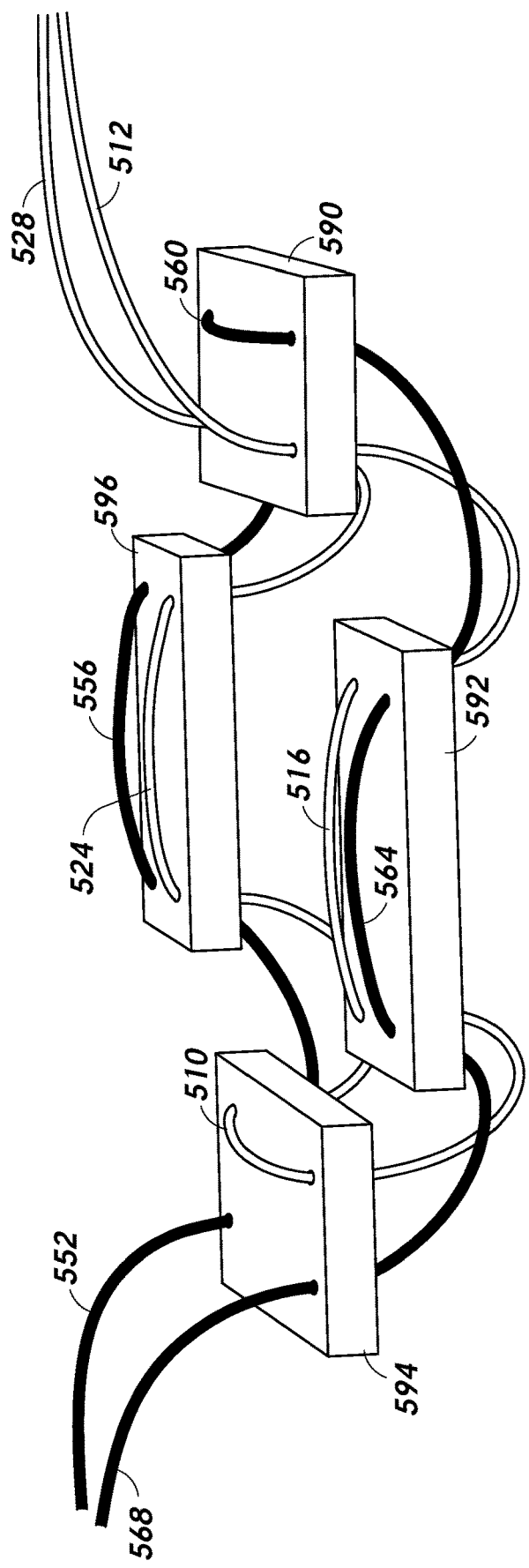
Figure 7C:
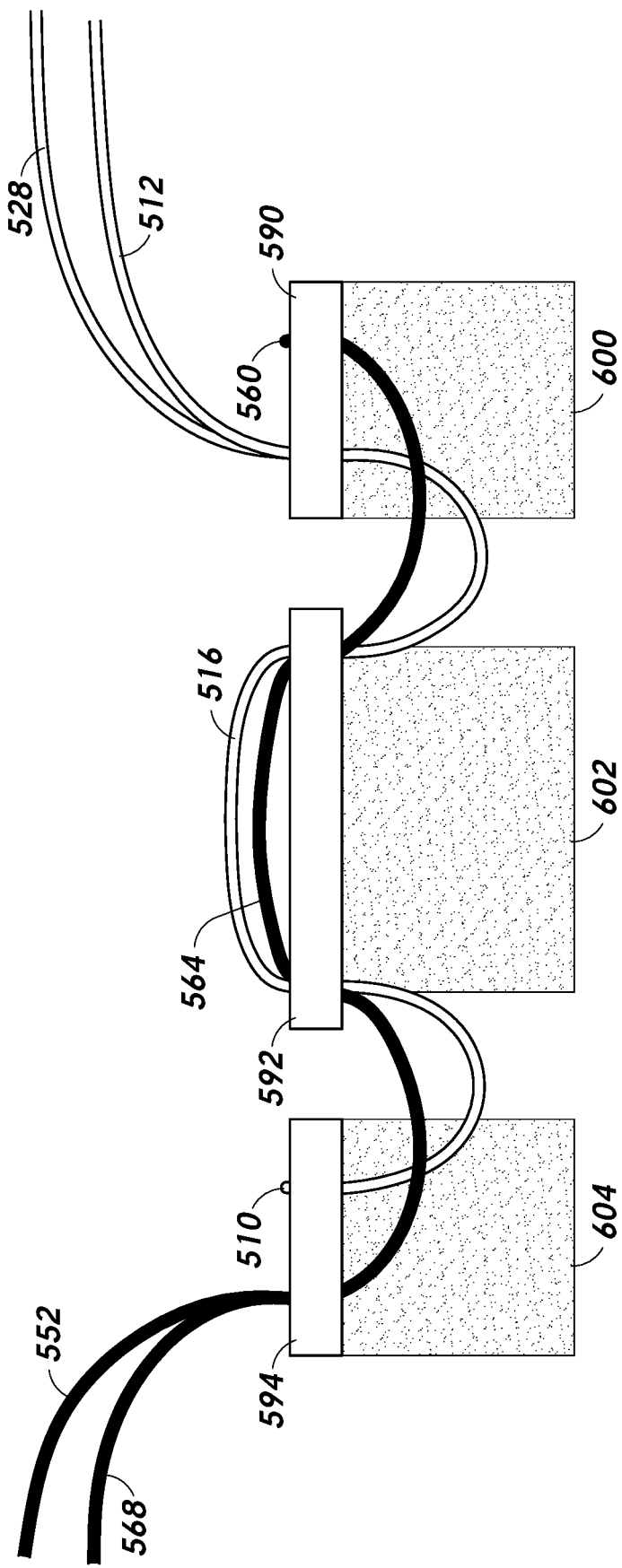

FIGS. 7A through 7C are a schematic plan view, perspective view and side view, respectively, of an example of a purse-string suture structure 500. The purse-string suture structure 500 can comprise a first purse-string suture 502 and a second purse-string suture 504 positioned around an opening in a target tissue, where both sutures 502, 504 are coupled to a first pad 590, a second pad 592, a third pad 594 and a fourth pad 596. The opening is marked by "X" in FIG. 7A. FIG. 7A is a plan view of the purse-string suture structure 500, while FIG. 7B is a perspective view and FIG. 7C is a side view. The second purse-string suture 504 can surround and be concentric with the first purse-string suture 502. The first purse-string suture 502 and/or the second purse-string suture 504 can have one or more of a circular, oval, and octagonal shape. In some instances, each of the first purse-string suture 502 and the second purse-string suture 504 can have a circular or substantially circular shape. In some instances, each of the first purse-string suture 502 and the second purse-string suture 504 can have an octagonal or substantially octagonal shape. As described herein, the purse-string suture structure 500 can be positioned in the heart wall for reducing a size and/or closing of an opening formed in the heart wall, such as that described with reference with FIG. 5. For example, the first purse-string suture 502 and second purse-string suture 504 can be threaded through the pericardium and one or more layers of the heart wall, including through at least a portion of the myocardium. For example, the first pad 590, second pad 592, third pad 594 and fourth pad 596 can be placed over the pericardium, including directly on and in contact with the pericardium. A lower surface of each of the pads 590, 592, 594, 596 can be oriented towards the pericardium and an upper surface of each of the pads 590, 592, 594, 596 can be oriented in an opposing direction away from the pericardium.

One or more of the pads 590, 592, 594, 596 can be aligned with a direction of a posterior mitral valve leaflet (PML). As shown in FIG. 7A, in some instances, the fourth pad 596 can be aligned with the direction of the posterior mitral valve leaflet (PML). In some instances, both the second pad 592 and the fourth pad 596 can be aligned with the direction of the posterior mitral valve leaflet (PML). For example, the second pad 592 and the fourth pad 596 can be at opposing positions relative to one another around the target opening such that both the second pad 592 and the fourth pad 596 can be aligned with the direction of the posterior mitral valve leaflet (PML). In some instances, the first pad 590 and the third pad 594 can be at opposing positions relative to one another. In some instances, the first pad 590 and the third pad 594 can be perpendicular or substantially perpendicular to the second pad 592 and the fourth pad 596. In some instances, the pads 590, 592, 594, 596 can be evenly distributed around the target opening, for example being equidistant from one another around the target opening. In some instances, the pads 590, 592, 594, 596 may not be evenly distributed around the target opening. In some instances, the positions of one or more of the pads 590, 592, 594, 596 can be predetermined based at least in part on a number of tethers and/or paths of the tethers, for example to provide desired orientations of the safe zones and/or number of safe zones for the tethers.

Referring to FIG. 7A, a first suture 510 can be used to stitch the first purse-string suture 502 along a first path around the opening and a second suture 550 can be used to stitch the second purse-string suture 504 along a second path around the opening. Each of the first pad 590, second pad 592, third pad 594 and fourth pad 596 can be at a first position, a second position, a third position and a fourth position around the target opening, respectively, along the first path and second path.

The first suture 510 can comprise: a first distal portion 512 coupled to the first pad 590, a first tissue portion 514 stitched through the target tissue and extending between the first pad 590 and the second pad 592 along the first path, a second pad portion 516 positioned over the second pad 592, including on and in contact with the second pad 592, a second tissue portion 518 stitched through the target tissue and extending between the second pad 592 and the third pad 594 along the first path, a third pad portion 520 positioned over the third pad 594, including on and in contact with the third pad 594, a third tissue portion 522 stitched through the target tissue and extending between the third pad 594 and the fourth pad 596, a fourth pad portion 524 positioned over the fourth pad 596, including on and in contact with the fourth pad 596, a fourth tissue portion 526 stitched through the target tissue and extending between the fourth pad 596 and the first pad 590, and a second distal portion 528 coupled to the first pad 590. The second suture 550 can comprise: a first distal portion 552 coupled to the third pad 594, a first tissue portion 554 stitched through the target tissue and extending between the third pad 594 and the fourth pad 596 along the second path, a fourth pad portion 556 positioned over the fourth pad 596, including on and in contact with the fourth pad 596, a second tissue portion 558 stitched through the target tissue and extending between the fourth pad 596 and the first pad 590 along the second path, a first pad portion 56o positioned over the first pad 590, including on and in contact with the first pad 590, a third tissue portion 562 stitched through the target tissue and extending between the first pad 590 and the second pad 592, a second pad portion 564 positioned over the second pad 592, including on and in contact with the second pad 592, a fourth tissue portion 566 stitched through the target tissue and extending between the second pad 592 and the third pad 594, and a second distal portion 568 coupled to the third pad 594. In some instances, the second pad portions 516, 564 can be parallel or substantially parallel to one another. In some instances, the fourth pad portions 524, 556 can be parallel or substantially parallel to one another. The first suture 510 and second suture 550 can be tensioned to form the first purse-string suture 502 and the second purse-string suture 504, respectively, around the target opening, for example, sealing the target opening and/or closing the target opening around a medical instrument and/or valve leaflet tether.

Each of the pads can provide a corresponding safe zone. For example, in FIG. 7A, a first safe zone 600 can extend into the tissue under the first pad 590, a second safe zone 602 can extend into the tissue under the second pad 592, a third safe zone 604 can extend into the tissue under the third pad 594, and a fourth safe zone 606 can extend into the tissue under the fourth pad 596. A height of each of the safe zones 600, 602, 604, 606 can be a distance into the target tissue which the respective safe zone extends. For example, the safe zones 600, 602, 604, 606 can have a height equal or similar to a thickness of the heart wall beneath the respective pad. The safe zones 600, 602, 604, 606 can each have a width similar or equal to a length of a suture portion positioned over a corresponding pad and/or a distance between positions at which distal ends of suture distal portions are located on the corresponding pad. In some instances, one or more of the safe zones 600, 602, 604, 606 can each have a width which is the shorter of the length of a suture portion positioned over a corresponding pad (e.g., a suture stitch) and the distance between positions at which distal ends of suture distal portions are located on the corresponding pad. In some instances, one or more of the safe zones 600, 602, 604, 606 can each have a width which is the shorter of the lengths of suture portions positioned over a corresponding pad. For example, the first safe zone 600 can have a width similar or equal to a shorter one of the length of the first pad portion 56o and the distance between the ends 532, 546. The second safe zone 602 can have a width similar or equal to a shorter one of the length of the second pad portions 516, 564. The third safe zone 604 can have a width similar or equal to a shorter one of the length of the third pad portion 520 and the distance between the ends 570, 584. The fourth safe zone 606 can have a width similar or equal to a shorter one of the length of the fourth pad portions 524, 556. The safe zones 600, 602, 604, 606 can extend across an entire width of a respective pad. For example, each of the safe zones 600, 602, 604, 606 can have a length, such as a dimension perpendicular or substantially perpendicular to the height and width of the respective safe zone, longer than a width of a corresponding rectangular pad as described herein. In some instances, the safe zones 600, 602, 604, 606 can extend from the opening in the target tissue to at least an outer edge of the purse-string suture structure 500.

In some instances, an orientation and/or length of the corresponding suture portions, and/or positions of the distal ends of suture distal portions on a respective pad can be selected to reduce or avoid irritation of the target tissue, and/or provide a desired size for the safe zones, while ensuring a secure attachment of the pads to the sutures. Referring to FIG. 7A, the first pad portion 560 can comprise distal ends 576, 578 and/or the distal portions 512, 528 can comprise distal ends 532, 546 at less than about 2 millimeters (mm) from respective nearest edge(s) of the first pad 590, including about 1 mm to about 2 mm from the respective nearest edge(s). The second pad portion 516 can comprise distal ends 534, 536 and the second pad portion 564 can comprise distal ends 580, 582 at less than about 2 millimeters (mm) from respective nearest edge(s) of the second pad 592, including about 1 mm to about 2 mm from the respective nearest edge(s). The third pad portion 520 can comprise distal ends 538, 540 and/or the distal portions 552, 568 can comprise distal ends 570, 584 at less than about 2 millimeters (mm) from respective nearest edge(s) of the third pad 594, including about 1 mm to about 2 mm from the respective nearest edge(s). The fourth pad portion 524 can comprise distal ends 542, 544 and the fourth pad portion 556 can comprise distal ends 572, 574 at less than about 2 millimeters (mm) from respective nearest edge(s) of the fourth pad 596, including about 1 mm to about 2 mm from the respective nearest edge(s). In some instances, suture portions positioned over the same pad can have the same or similar length. In some instances, a length of a suture portion can be the same as or similar to a distance between distal ends of distal portions coupled to the same pad.

In some instances, the four pads 590, 592, 594, 596 each can have a rectangular shape, where a longer edge of the rectangles can be oriented toward the opening in the target tissue, while an opposing longer edge can be oriented away from the opening. Shorter edges of the rectangles can extend between the longer edges. In some instances, corresponding portions of the first suture 510 positioned over the pads can extend along a path less than about 2 millimeters (mm) from a respective longer edge which is closer to the opening in the target tissue. In some instances, corresponding portions of the second suture 550 positioned over the pads can along a path less than about 2 millimeters (mm) from a respective longer edge which is farther away from the opening in the target tissue. In some instances, distal ends of the suture portions positioned over the pads can be at locations on the pad less than about 2 millimeters (mm) from a respective nearest shorter edge of the corresponding pad. In some instances, distal ends of the distal portions can be less than about 2 millimeters (mm) from one or both of the nearest longer edge (e.g., one of the longer edge closer to the opening and the longer edge farther away from the opening) and nearest shorter edge of the respective pad. In some instances, a pad can have a rounded shape, for example comprising an arcuate edge, such that an end of a suture portion is positioned less than about 2 millimeters (mm) from one nearest edge.

A method of forming the first purse-string suture 502 and second purse-string suture 504 can comprise coupling each of the pads 590, 592, 594, 596 to the first suture 510 and second suture 550. In some instances, the first suture 510 can be stitched to each of the pads 590, 592, 594, 596 prior to coupling the second suture 550 to each of the pads 590, 592, 594, 596. In some instances, the first suture 510 can be coupled to the fourth pad 596. For example, the first suture 510 can be threaded through the fourth pad 594 to position a stitch, such as the fourth pad portion 524, over the fourth pad 596. Subsequently, the first suture 510 can be stitched through the target tissue from each of two sides, such as two opposing sides, of the fourth pad 594 along the first path toward the position for the third pad 594 and the position for the first pad 590 such that the third tissue portion 522 and the fourth tissue portion 526 can be formed, respectively. The first suture 510 can then be coupled to the third pad 594 and the first pad 590. The first suture 510 can be threaded through the first pad 590 such that the second distal portion 528 can be coupled to the first pad 590. The first suture 510 can be stitched to the third pad 594 to position the third pad portion 520 over the third pad 594. Subsequently, the second tissue portion 518 can be formed in the target tissue by threading the first suture 510 through the target tissue from the position for the third pad 594 toward the position for the second pad 592 along the first path. The second pad 592 can be coupled to the first suture 510 to position the second pad portion 516 over the pad. The first suture 510 can be extended along the first path through the target tissue from the second pad 592 to the position for the first pad 590 to form the first tissue portion 514. The first suture 510 can then be threaded through the first pad 590 to couple the first distal portion 512 to the first pad 590.

A method of forming the second purse-string suture 504 can comprise coupling the second suture 550 to the fourth pad 596. The second suture 550 can be threaded through the fourth pad 594 to position a stitch, such as the fourth pad portion 556, over the fourth pad 596. Subsequently, the second suture 550 can be stitched through the target tissue from each of two sides, such as opposing sides, of the fourth pad 594 along the second path toward the position for the third pad 594 and the position for the first pad 590 such that the first tissue portion 554 and the second tissue portion 558 can be formed, respectively. The second suture 550 can then be coupled to the third pad 594 and the first pad 590. The second suture 550 can be threaded through the third pad 594 such that the first distal portion 552 can be coupled to the third pad 594. The second suture 550 can be stitched to the first pad 590 to position the first pad portion 56o over the first pad 590. Subsequently, the third tissue portion 562 can be formed in the target tissue by threading the second suture 550 through the target tissue from the position for the first pad 590 toward the position for the second pad 592 along the second path. The second pad 592 can be coupled to the second suture 550 to position the second pad portion 564 over the pad. The second suture 550 can be extended along the second path through the target tissue from the second pad 592 to the position for the third pad 594 to form the fourth tissue portion 566. The second suture 550 can then be coupled to the third pad 594. The second suture 550 can be threaded through the third pad 594 to couple the second distal portion 568 to the third pad 594.

Referring to FIG. 7B, a schematic perspective view of the purse-string suture structure 500 is shown. Portions of the first suture 510 and second suture 550 positioned over each of the pads 590, 592, 594, 596 are shown. As described herein, positioning portions of the sutures 510, 550 over the pads 590, 592, 594, 596 can facilitate providing safe zones beneath the pads. Referring to FIG. 7C, a schematic side view of the purse-string suture structure 500 is shown. The first pad 590, second pad 592 and third pad 594, and the corresponding safe zones 600, 602 and 604 are shown in FIG. 7C. The pads 590, 592, 594 can be positioned over the target tissue, such as directly on and in contact with the target tissue, such as the heart wall. As described herein, the safe zones below the first pad 590, second pad 592 and third pad 594 can extend into the target tissue. In some instances, the safe zone 602 can have a width similar or equal to a length of the second pad portion 516 and/or the second pad portion 564 positioned over the second pad 592. In some instances, the safe zone 602 can have a width which is the shorter of the length of the second pad portion 516 and the length of the second pad portion 564. In some instances, the safe zones 600, 604 can have a length, such as a dimension perpendicular or substantially perpendicular to the width of the respective safe zone, longer than a width of the corresponding pad. For example, the safe zones 600, 604 can have a length at least as long as a width of the first pad 590 and third pad 594, respectively. In FIG. 7C, only the portions of the safe zones 600, 604 under the respective pads are shown. Note that, for simplicity, details of the stitching through the tissue between the pads is not shown in FIGS. 7B and 7C.

As described herein, the distal portions of the sutures can be arranged in a number of different manners relative to the four pads, and are not limited to the example described with reference to FIGS. 7A to 7C. Respective distal portions of the sutures can be coupled to the same one of the four pads, or to two of the four pads different from those described herein. The combination shown in FIGS. 7A to 7C is used for illustrative purposes only.

One or more purse-string sutures as described herein can be formed on the heart wall, including on an apex region of the heart wall. In some instances, the purse-string sutures can be formed on a heart wall to seal an opening used to access the mitral valve, such as to perform a mitral valve repair procedure. In some instances, the mitral valve repair procedure can comprise deploying a tether to a mitral valve leaflet to tether the leaflet to the heart wall. For example, the procedure can comprise deploying a tether to a posterior mitral valve leaflet and coupling the posterior mitral valve leaflet to the heart wall using the tether. In some instances, one or more purse-string sutures can be formed on an antero-lateral portion of the left ventricular heart wall. The purse-string sutures can be formed to seal the left ventricle from the external environment, such as one or more purse-string sutures as described herein. For example, the sutures can be stitched through the pericardium, epicardium and at least a portion of the myocardium. Access to the heart can be achieved transapically, such as by performing a left thoracotomy (e.g., between the fourth or fifth intercostal space). As described herein, a purse-string suture structure can comprise one or more purse-string sutures, including two, three or four concentric purse-string sutures.

Figure 8:
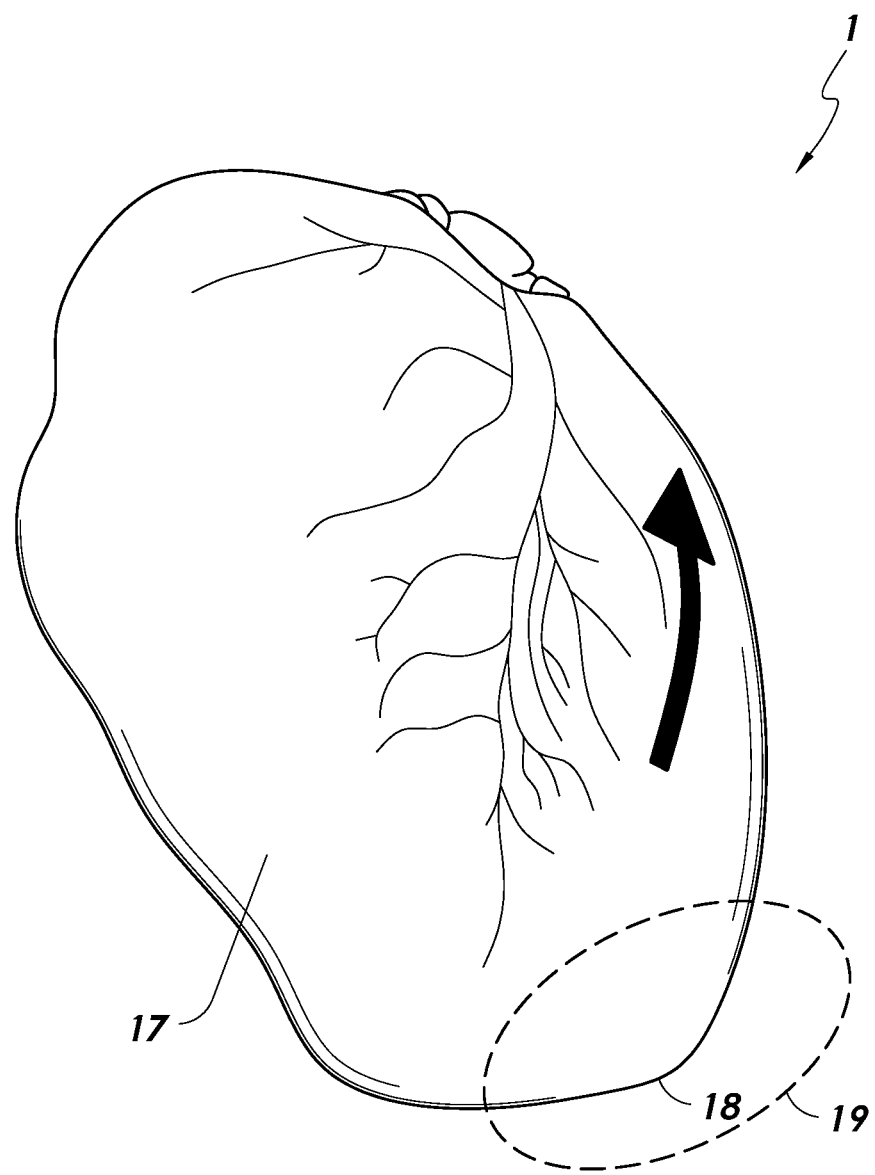
FIG. 8 shows a heart and a direction of a posterior mitral valve leaflet (PML) marked thereon, according to some instances.

In some instances, a method for forming a purse-string suture structure can comprise identifying a direction of a posterior mitral valve leaflet (PML). Referring to FIG. 8, a schematic is shown of the heart 1 and a direction of a posterior mitral valve leaflet (PML) marked thereon. The direction of the posterior mitral valve leaflet (PML) is marked using a bold arrow in the figure. A process for forming a purse-string suture around an opening on the heart wall 17 can comprise identifying the posterior mitral valve leaflet (PML) direction and marking the direction on the exterior of the heart 1. The posterior mitral valve leaflet (PML) direction can be marked based on the location of the opening formed in the target tissue. For example, the opening can be formed on the heart wall 17 for tethering a posterior mitral valve leaflet to the heart wall 17. In some instances, the opening can be formed in the apex region 19. In some instances, the opening can be formed about 2 centimeters (cm) lateral of the left anterior descending artery (LAD) and about 2 cm to about 3 cm basal from the apex 18 of the heart 1. The mark for the posterior mitral valve leaflet (PML) direction can be selected at a location having a desired distance from the opening while in alignment with the direction of the leaflet. One or more of the plurality of pads of the purse-string suture structure can be aligned with the posterior mitral valve leaflet (PML) direction. In some instances, one of the plurality of pads can be aligned and positioned over the marked arrow indicating the posterior mitral valve leaflet (PML) direction.

FIGS. 9A through 9D show portions of an example of a process for forming the purse-string suture structure 300 described with reference to FIG. 6A. As shown in FIGS. 9A through 9D, stitching for an inner purse-string suture, such as the first purse-string suture 302, can be formed prior to stitching an outer purse-string suture, such as the second purse-string suture 304. The first suture 310 and second suture 340 can comprise a variety of materials. In some instances, the first suture 310 and/or the second suture 340 can be a polypropylene suture (e.g., Prolene® sutures, including Ethicon® 3-0 Prolene® sutures).

Figure 9A:
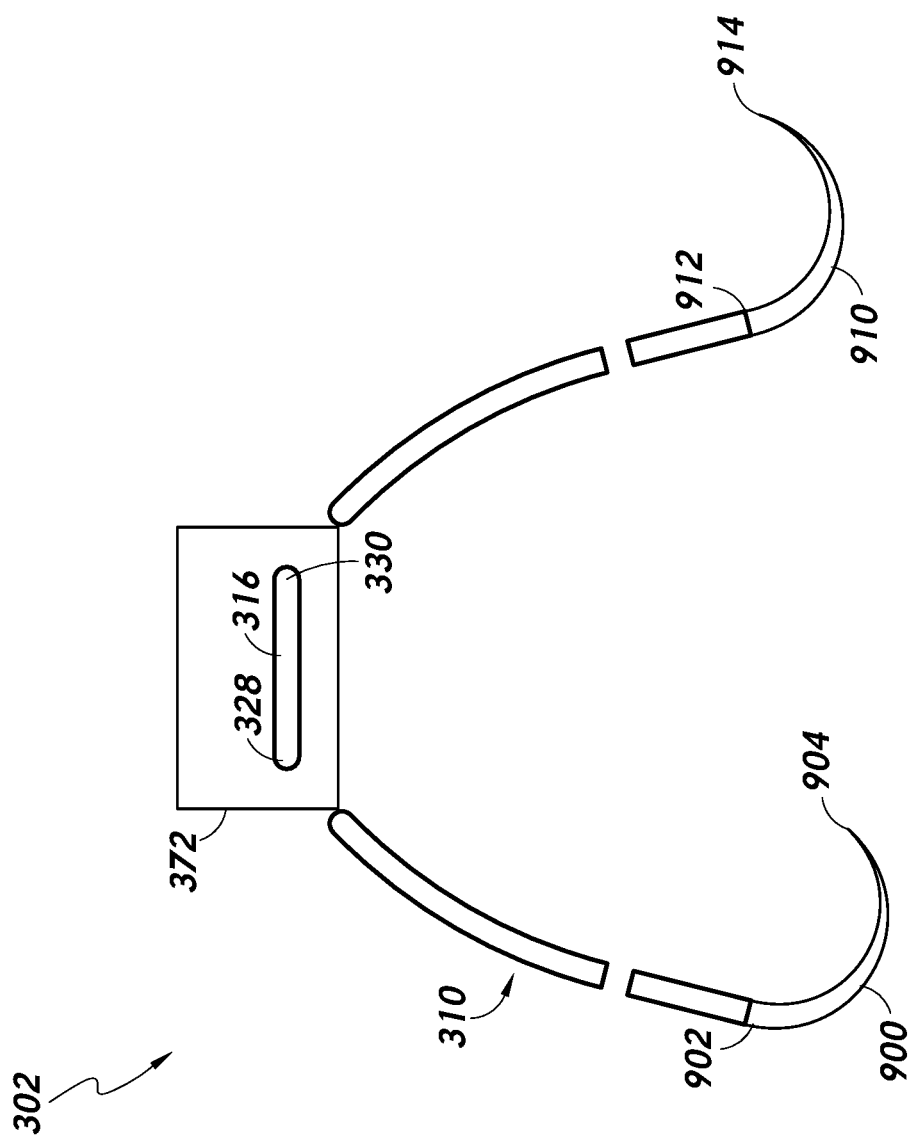
FIGS. 9A through 9D show an example of a process for forming the purse-string suture structure described with reference to FIG. 6A, according to some instances.

Referring to FIG. 9A, a first needle 900 and a second needle 910 can be provided for forming the first purse-string suture 302. Each of the first needle 900 and second needle 910 can comprise a curvature. For example, the needles 900, 910 can be curved needles. Respective first ends 902, 912 of each of the first needle 900 and second needle 910 can be configured to be coupled to opposing ends of the first suture 310. Respective second ends 904, 914 of the first needle 900 and second needle 910 can be sharp ends, for example being configured to pierce the target tissue and/or pads. In some instances, the first needle 900 and the second needle 910 can comprise a taper which tapers toward the respective second ends 904, 914 of the needles 900, 910. In some instances, the curved needle can have a semi-circular shape (e.g., Ethicon® tapered SH 26 mm ½C).

The first suture 310 can be coupled to the second pad 372. For example, the first suture 310 can be threaded through the second pad 372 such that a suture stitch, for example the second pad portion 316, can be positioned over the second pad 372. The first suture 310 can be threaded through a first location and a second location on the second pad 372 to position the second pad portion 316 over an upper surface of the second pad 372. In some instances, the first needle 900 can be threaded from the upper surface through to the lower surface of the second pad 372 at the first location and the second needle 910 can be threaded from the upper surface through to the lower surface of the second pad 372 at the second location such that the second pad portion 316 can be positioned over the upper surface of the second pad 372. The first and second locations can be selected such that the distal ends 328, 330 of the second pad portion 316 are positioned less than about 2 millimeters from nearest edges of the second pad 372. In some instances, the second pad portion 316 can extend along a path which is less than about 2 millimeters (mm) from a nearest edge of the second pad 372. For example, the second pad portion 316 can extend along a path less than about 2 mm from an edge of the second pad 372 configured to be positioned closer to the opening in the target tissue, such as an inner edge of the second pad 372, including a longer edge of the second pad 372 configured to be oriented closer to the opening in the target tissue. In some instances, the distal ends 328, 330 can be positioned less than about 2 millimeters (mm) from opposing ends of the second pad 372. In some instances, the distal ends 328, 330 can be positioned less than about 2 millimeters (mm) from a respective one of opposing shorter edges of the second pad 372. In some instances, the distal ends 328, 330 can be positioned less than about 2 millimeters (mm) from the longer edge of the second pad 372 configured to be oriented closer to the opening.

Figure 9B:
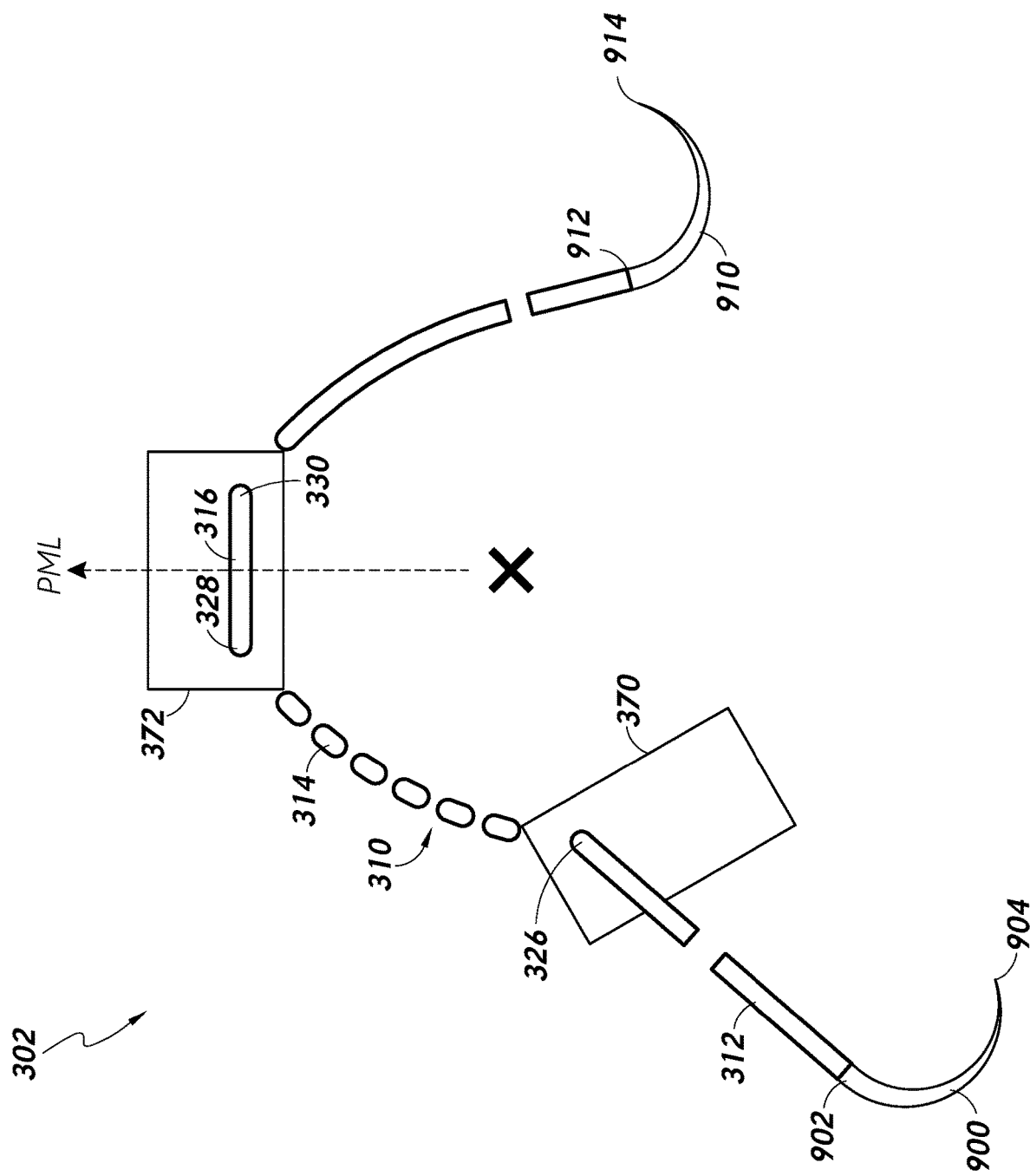

Referring to FIG. 9B, the second pad 372 can be positioned over a desired position over the target tissue. For example, the second pad 372 can be positioned at the second position along the first path around the opening. In some instances, the second pad 372 can be oriented such that it aligns with the posterior mitral valve leaflet (PML) direction. For example, the second pad 372 can be positioned over the marked line indicating the posterior mitral valve leaflet (PML) direction. The second pad 372 can then be stitched to the second position. The first needle 900 can subsequently be used to thread the first suture 310 from the second pad 372 to the position of the first pad 370. The first suture 310 can be stitched through the target tissue to extend from the second pad 372 to the first pad 370 along the first path so as to form the first tissue portion 314. In some instances, the first path between the second pad 372 and the first pad 372 can be parallel or substantially parallel the left anterior descending artery (LAD). In some instances, the first path between the second pad 372 and the first pad 372 can be selected to avoid anatomical elements, such as left anterior descending artery (LAD) branches.

The first suture 310 can then be coupled to the first pad 370. For example, the first needle 900 can be used to thread the first suture 310 through a first location on the first pad 370 from a lower surface to an upper surface of the first pad 370. The first suture 310 can be extended through the first pad 370 such that the first distal portion 312 can be coupled to the first pad 370. The first location on the first pad 370 can be selected such that a distal end 326 of the first distal portion 312 is positioned less than about 2 millimeters (mm) from a nearest edge of the first pad 370. In some instances, the distal end 326 can be positioned less than about 2 millimeters (mm) from a nearest shorter edge of the first pad 370 and/or less than about 2 millimeters (mm) from the longer edge of the first pad 370 configured to be oriented closer to the opening.

Figure 9C:
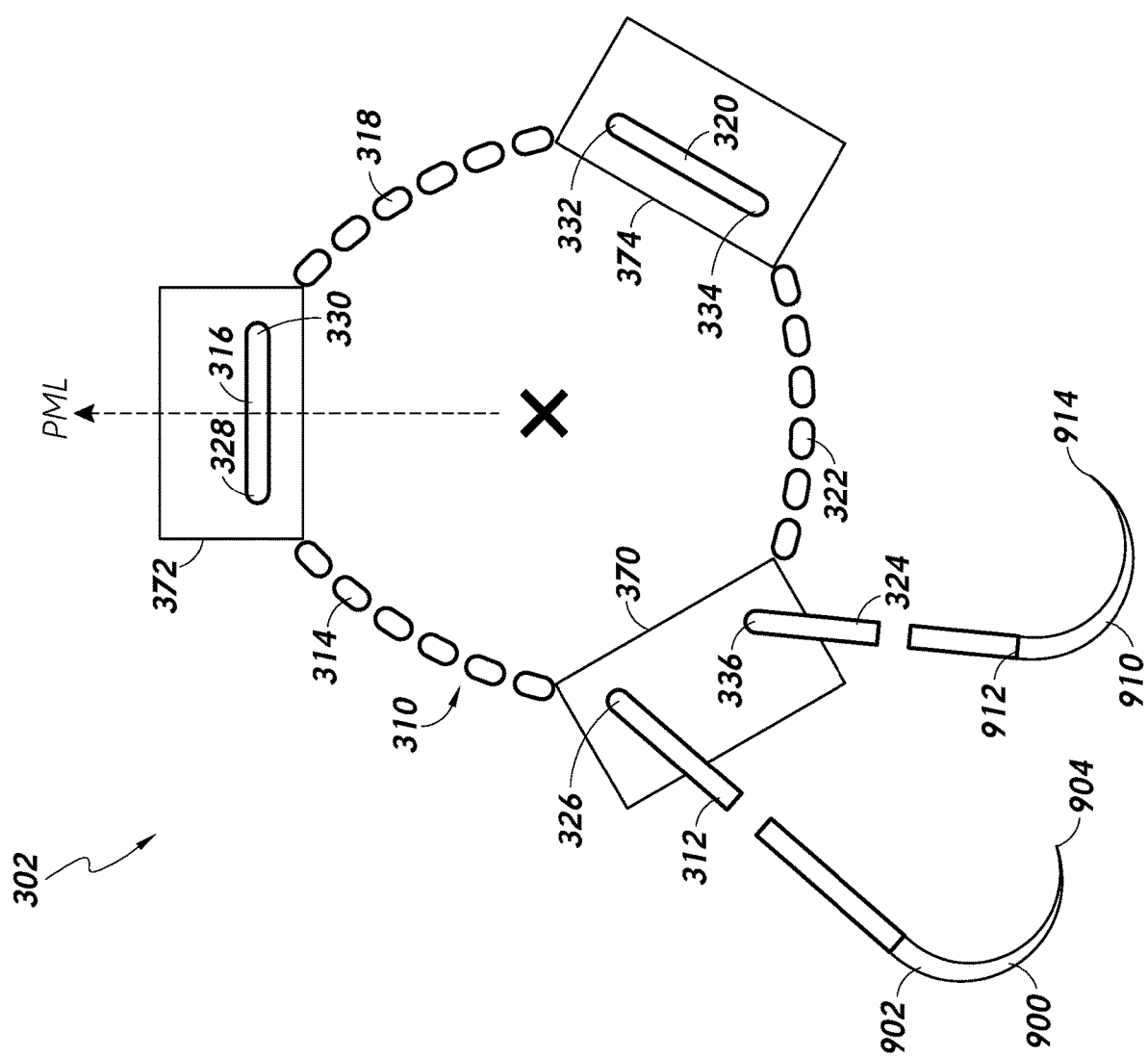

In FIG. 9C, the second needle 910 can be used to thread the first suture 310 through the target tissue from the second pad 372 to the third pad 374. The first suture 310 can be stitched through the target tissue from the second pad 372 to the third pad 374 along the first path, so as to form the second tissue portion 318. The first suture 310 can then be coupled to the third pad 374. For example, the first suture 310 can be threaded through the third pad 374 such that a third pad portion 320 of the first suture 310 can be positioned over the upper surface of the third pad 374. The first suture 310 can be threaded through a first location on the third pad 374 from the lower surface through to the upper surface of the third pad 374, and through a second location on the third pad 374 from the upper surface through to the lower surface, so as to position the third pad portion 320 over the upper surface of the third pad 374. In some instances, the third pad portion 320 can extend along a path which is less than about 2 millimeters (mm) from a nearest edge of the third pad 374, such as a longer edge of the third pad 374 configured to be positioned closer to the opening in the target tissue, including an inner longer edge of the third pad 374 oriented closer to the opening in the target tissue. In some instances, the distal ends 332, 334 of the third pad portion 320 can be positioned less than about 2 millimeters (mm) from respective nearest edges of the third pad 374, including from opposing edges of the third pad 374. For example, the distal ends 332, 334 can be positioned less than about 2 millimeters (mm) from a respective one of opposing shorter edges of the third pad 374. In some instances, the distal ends 332, 334 can be positioned less than about 2 millimeters (mm) from the longer edge of the third pad 374 configured to be oriented closer to the opening.

The third pad 374 can be positioned at a predetermined position along the first path. In some instances, the third pad 374 can be positioned at a third position such that the first pad 370, second pad 372 and third pad 374 are evenly distributed around the opening in the target tissue, for example evenly distributed around the first path surrounding the target opening.

The first suture 310 can subsequently be stitched using the second needle 910 through the target tissue from the third pad 374 to the position of the first pad 370. The first suture 310 can be threaded through the target tissue to form the third tissue portion 322 along the first path. The first suture 310 can then be coupled to the first pad 370 to surround the opening in the target tissue. In some instances, the first suture 310 can be threaded through a second location on the first pad 370, for example from the lower surface through to the upper surface of the first pad 370, such that the second distal portion 324 of the first suture 310 can be coupled to the first pad 370. The second location on the first pad 370 can be selected such that a distal end 336 of the second distal portion 324 is positioned less than about 2 millimeters (mm) from one or more edges of the first pad 370. In some instances, the distal end 336 can be positioned less than about 2 millimeters (mm) from a nearest shorter edge of the first pad 370 and/or less than about 2 millimeters (mm) from the longer edge of the first pad 370 configured to be oriented closer to the opening.

Figure 9D:
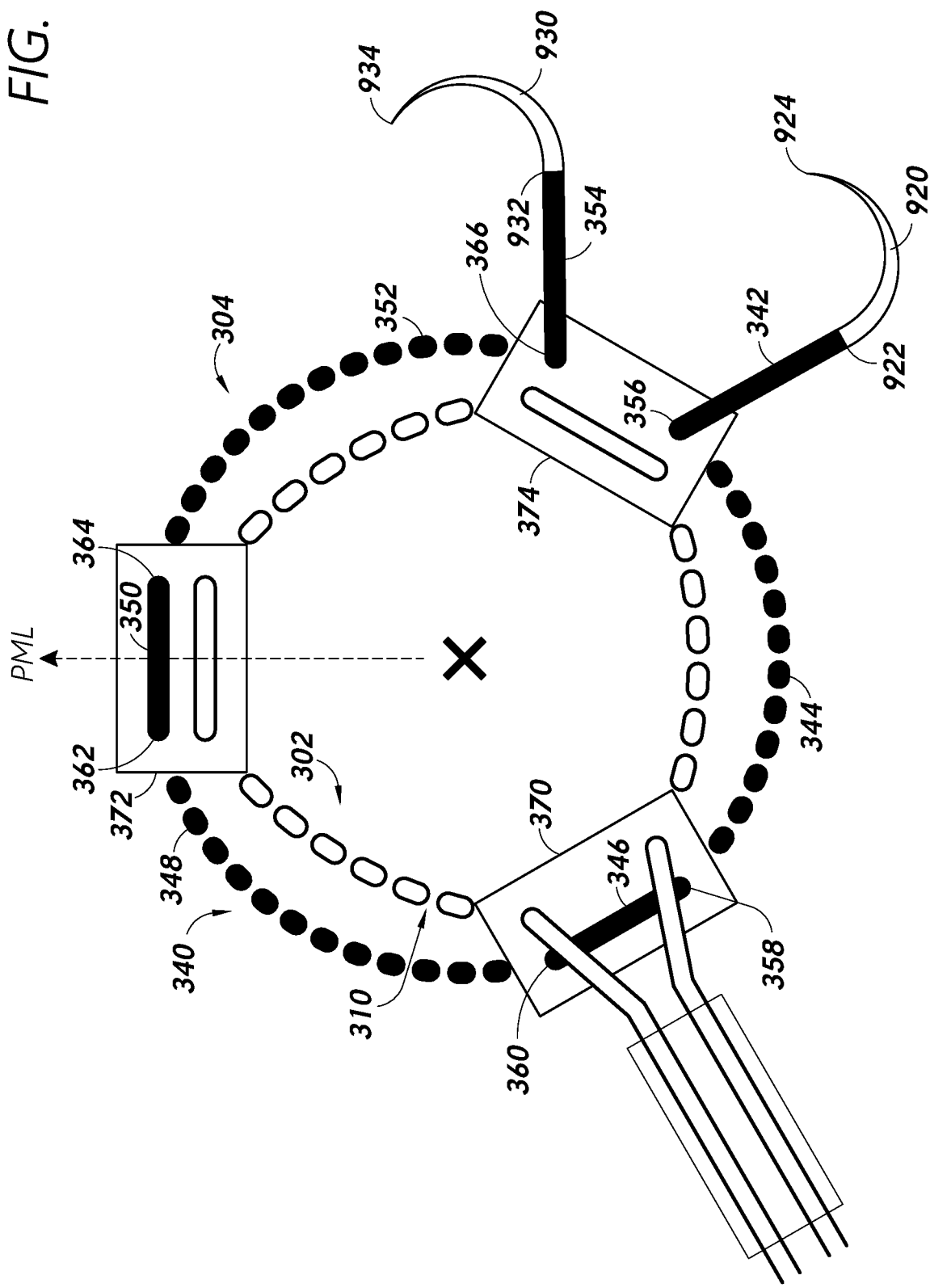

FIG. 9D shows the second purse-string suture 304 formed in the target tissue to be around and concentric with the first purse-string suture 302. In some instances, the second purse-string suture 304 can be formed after stitching for the first purse-string suture 302 is completed. The second purse-string suture 304 can be formed around the first purse-string suture 302 such that the second purse-string suture 304 surrounds and is concentric with the first purse-string suture 302. As shown in FIG. 9D, the first distal portion 342 and second distal portion 354 of the second suture 340 can be coupled to the third pad 374. As described herein, the first distal portion 312 and the second distal portion 324 of the first suture 310 can be coupled to the first pad 370.

A third needle 920 and a fourth needle 930 can be coupled to opposing ends of the second suture 340. The third needle 920 and/or the fourth needle 930 can comprise one or more characteristics of the first needle 900 and/or second needle 910. For example, each of the third needle 920 and fourth needle 930 can be a curved needle comprising a taper which tapers toward respective second ends 924, 934. Respective first ends 922, 932 of each of the third needle 920 and fourth needle 930 can be configured to be coupled to the opposing ends of the second suture 340, and respective second ends 924, 934 of the third needle 920 and fourth needle 930 can be sharp ends.

In some instances, forming the second purse-string suture 304 can comprise coupling the second suture 340 to the first pad 370. The third needle 920 and fourth needle 930 can be used to thread the second suture 340 through the first pad 370 to position a first pad portion 346, such as a stitch, of the second suture 340 over the upper surface of the first pad 370. For example, the second suture 340 can be threaded at a third location from the upper surface through to the lower surface of the first pad 370 using the third needle 920, and at a fourth location from the upper surface through to the lower surface of the first pad 370 using the fourth needle 930. The third and fourth locations can be selected such that the distal ends 358, 360 of the first pad portion 346 are positioned less than about 2 millimeters from respective nearest edges of the first pad 370. In some instances, the distal ends 358, 360 can be positioned less than about 2 millimeters (mm) from opposing ends of the first pad 370. In some instances, the first pad portion 346 can extend along a path which is less than about 2 millimeters (mm) from a nearest edge of the first pad 370, such as from an edge of the first pad 370 configured to be positioned away from the opening in the target tissue, such as an outer edge of the first pad 370. For example, the first pad portion 346 can be positioned along a path less than about 2 millimeters (mm) from a longer edge of the first pad 370 configured to be oriented away from the opening. In some instances, the distal ends 358, 360 can be positioned less than about 2 millimeters (mm) from a respective nearest shorter edge of the first pad 370.

The third needle 920 can then be used to thread the second suture 340 through the target tissue from the first pad 370 to the position of the third pad 374 along the second path, so as to form the first tissue portion 344. The second suture 340 can subsequently be coupled to the third pad 374. In some instances, the second suture 340 can be threaded through a third location on the third pad 374, for example from the lower surface through to the upper surface of the third pad 374, such that the first distal portion 342 of the second suture 340 can be coupled to the third pad 374. The third location on the third pad 374 can be selected such that a distal end 356 of the first distal portion 342 is positioned less than about 2 millimeters (mm) from one or more edges of the third pad 374. In some instances, the distal end 356 can be positioned less than about 2 millimeters (mm) from a nearest shorter edge of the third pad 374 and/or less than about 2 millimeters (mm) from the longer edge of the third pad 374 configured to be oriented farther away from the opening.

In some instances, the second suture 340 can be threaded through the target tissue using the fourth needle 930 to extend from the first pad 370 to the position of the second pad 372 along the second path to form the second tissue portion 348. The second suture 340 can be coupled to the second pad 372. The second suture 340 can be threaded through a third location and a fourth location on the second pad 372 to position the second pad portion 350 over the upper surface of the second pad 372. In some instances, the fourth needle 930 can be threaded from the lower surface through to the upper surface of the second pad 372 at the third location and from the upper surface through to the lower surface of the second pad 372 at the fourth location to position the second pad portion 350 over the upper surface of the second pad 372. The third and fourth locations can be selected such that the distal ends 362, 364 of the second pad portion 350 are positioned less than about 2 millimeters from respective nearest edges of the second pad 372, such as from opposing edges of the second pad 372. In some instances, the second pad portion 350 can extend along a path which is less than about 2 millimeters (mm) from a nearest edge of the second pad 372, such as an edge configured to be positioned away from the opening in the target tissue, including an outer edge of the second pad 372. For example, the second pad portion 350 can be positioned along a path less than about 2 millimeters (mm) from a longer edge of the second pad 372 configured to be oriented away from the opening. The distal ends 362, 364 can be positioned less than about 2 millimeters (mm) from a respective nearest shorter edge of the second pad 372.

The fourth needle 930 can then be used to stitch the second suture 340 through the target tissue from the second pad 372 to the position of the third pad 374 along the second path, so as to form the third tissue portion 352. The second suture 340 can subsequently be coupled to the third pad 374, such as by threading the second suture 340 through a fourth location on the third pad 374. The second suture 340 can be threaded from the lower surface through to the upper surface of the third pad 374, such that the second distal portion 354 of the second suture 340 can be coupled to the third pad 374. The fourth location on the third pad 374 can be selected such that a distal end 366 of the second distal portion 354 is positioned less than about 2 millimeters (mm) from one or more edges of the third pad 374. In some instances, the distal end 366 can be positioned less than about 2 millimeters (mm) from a nearest shorter edge of the third pad 374 and/or less than about 2 millimeters (mm) from the longer edge of the third pad 374 configured to be oriented farther away from the opening.

The order in which the first suture 310 and/or the second suture 340 are coupled to one or more of the pads and/or are stitched through the target tissue can be different from the sequence as described herein. In some instances, first suture 310 can be coupled to the first pad 370 or the third pad 374 prior to being coupled to the second pad 372. In some instances, the second suture 340 can be coupled to the second pad 372 or the third pad 374 prior to being coupled to the first pad 370.

Figure 10:
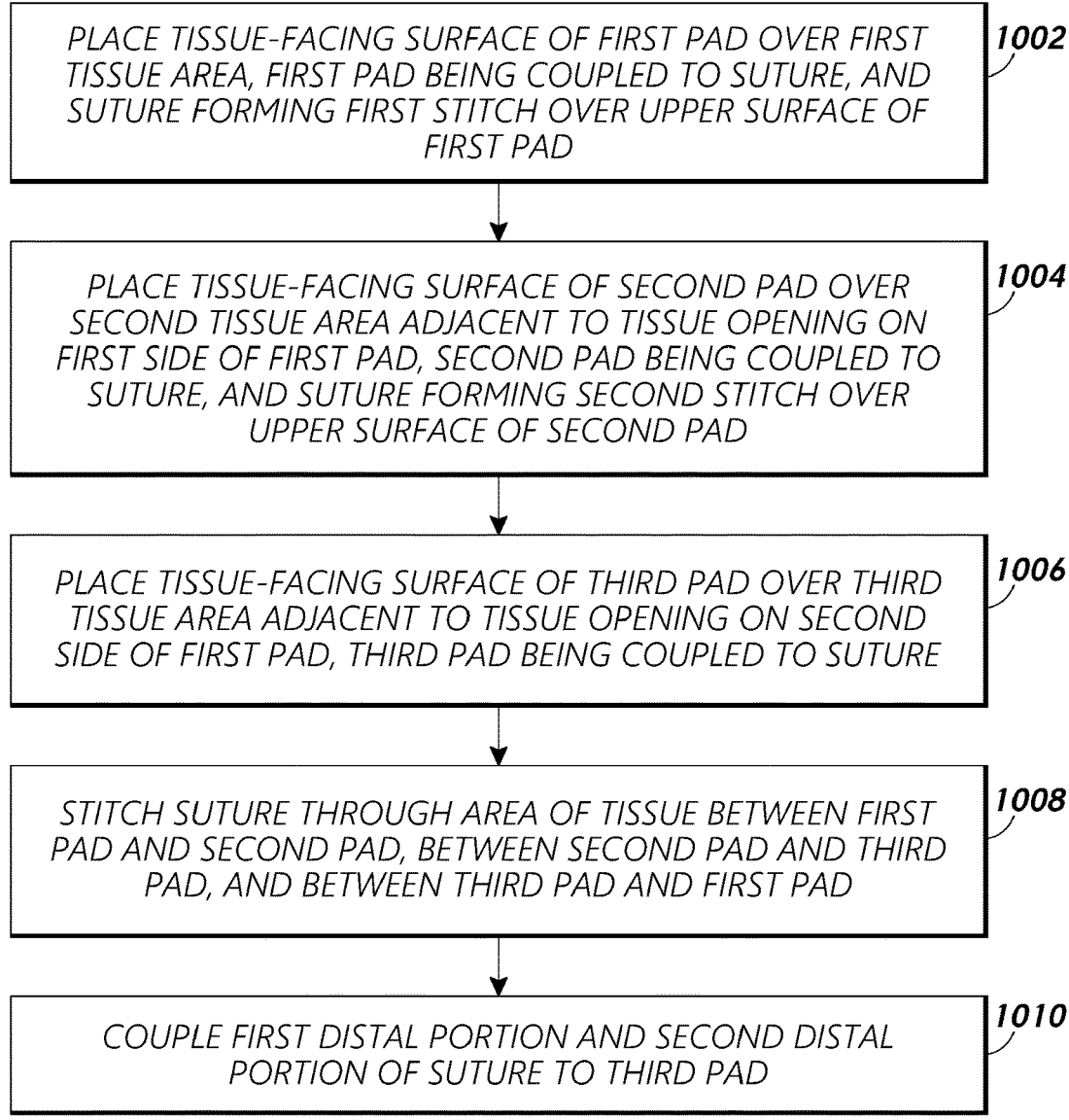
FIG. 10 is a flow diagram of an example of a process for forming a purse-string suture around an opening in a target tissue, according to some instances.

As described herein, a purse-string suture structure can comprise one or more purse-string sutures. In some instances, a purse-string suture structure can comprise one purse-string suture. In some instances, the one purse-string suture can comprise a suture coupled to three or more pads. FIG. 10 is flow diagram of an example of a process 1000 for forming a purse-string suture around an opening in a target tissue. At block 1002, the process 1000 can involve placing a tissue-facing surface of a first pad over a first tissue area adjacent to the tissue opening. The first pad can be coupled to a suture. The suture can be used to stitch the purse-string suture around the opening. The suture can form a first stitch over the upper surface of the first pad. At block 1004, the process 1000 can involve placing a tissue-facing surface of the second pad over a second tissue area adjacent to the tissue opening on a first side of the first pad. The second pad can be coupled to the suture, and the suture can form a second stitch over the upper surface of the second pad. At block 1006, the process 1000 can involve placing a tissue-facing surface of a third pad over a third tissue area adjacent to the tissue opening on a second side of the first pad. The third pad can be coupled to the suture. In some instances, an orientation and/or length of the corresponding stitch portions positioned over the pads can be predetermined to reduce or avoid irritation of the target tissue, and/or provide a desired size for the safe zones, while ensuring a secure attachment of the pads to the suture. For example, one or more of the stitch portions can have distal ends positioned at less than about 2 millimeters (mm) from the nearest respective edges of the pad. In some instances, the suture can be coupled to the third pad at positions on the pad which are less than about 2 millimeters (mm) from the nearest edges of the pad.

At block 1008, the process 1000 can involve stitching the suture through an area of tissue between the first pad and the second pad, through an area of tissue between the second pad and the third pad, and through an area of tissue between the third pad and the first pad. The suture can be threaded through the target tissue to connect the three pads. At block 1010, the process 1000 can involve coupling a first distal portion and a second distal portion of the suture to the third pad for forming the purse-string suture. The distal portions can be tensioned to form the purse-string suture, including to close and/or seal the opening using the purse-string suture.

In some instances, the target tissue can be heart tissue. For example, placing the first pad, second pad and third pad over the respective tissue areas can comprise positioning the pads over a pericardium of the heart. In some instances, the pads can be positioned around an opening formed in an apex region of the heart. In some instances, one or more of the plurality of pads can be aligned with the posterior mitral leaflet.

Figure 11:
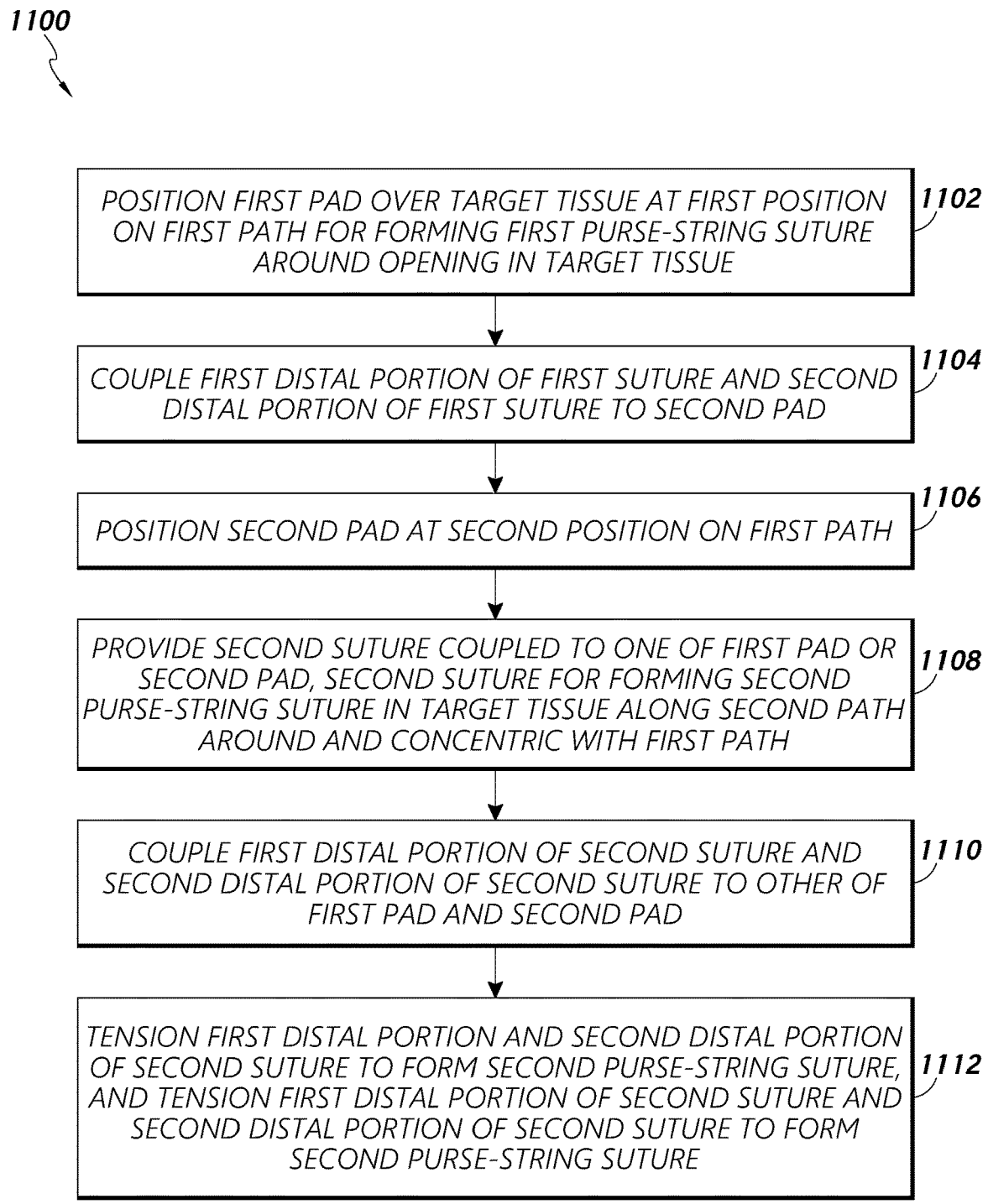
FIG. 11 is a flow diagram of an example of a process for forming two purse-string sutures around an opening in a target tissue, according to some instances.

FIGS. 11 and 12 are flow diagrams showing examples of processes for forming a first purse-string suture and a second purse-string suture around an opening in a target tissue. In the processes described with reference to FIGS. 11 and 12, a first suture can be used to stitch the first purse-string suture and a second suture can be used to stitch the second purse-string suture in the target tissue around the opening along a first path and a second path, respectively. The second path can surround and be concentric with the first path. A plurality of pads can be stitched to the first purse-string suture and second purse-string suture and positioned over the target tissue. For example, a lower surface of each of the plurality of pads can be configured to be oriented toward the target tissue and an upper surface of each of the plurality of pads can be configured to be oriented away from the target tissue. As described herein, the target tissue can be heart tissue. In some instances, positioning one or more of the plurality of pads can comprise positioning a pad over a pericardium of the heart. In some instances, one or more of the plurality of pads can be positioned around an opening formed in an apex region of the heart. For example, the plurality of pads can be positioned directly on and in contact with the pericardium around an opening formed in the apex region of the heart. In some instances, one or more of the plurality of pads can be aligned with the posterior mitral leaflet.

Referring to FIG. 11, an example of a process 1100 for forming the first and second purse-string sutures around an opening in a target tissue is shown. In block 1102, the process 1100 can involve positioning a first pad over a target tissue at a first position on the first path for forming the first purse-string suture around the opening. In some instances, the first pad can be positioned such that it is aligned with a direction of the posterior mitral leaflet. The first pad can be coupled to the first suture. A first corresponding portion of the first suture can be positioned over an upper surface of the first pad.

In block 1104, the process 1100 can involve coupling a first distal portion of the first suture and a second distal portion of the first suture to a second pad. In block 11o6, the process 1100 can involve positioning the second pad at a second position on the first path. In some instances, the second pad can be positioned at an opposing location along the first path from that of the first pad.

In block 11o8, the process 1100 can involve providing the second suture coupled to one of the first pad and the second pad, the second suture for forming a second purse-string suture in the target tissue along a second path around and concentric with the first path. A first corresponding portion of the second suture can be positioned over an upper surface of the one of the first pad and the second pad.

In block 1110, the process 1100 can involve coupling a first distal portion of the second suture and a second distal portion of the second suture to the other of the first pad and the second pad. In block 1112, the process 1100 can involve tensioning the first distal portion and second distal portion of the first suture to form the first purse-string suture, and tensioning the first distal portion of the second suture and second distal portion of the second suture to form the second purse-string suture.

In some instances, a third pad can be positioned over the target tissue at a third position on the first path. The third pad can be coupled to the first suture and a third corresponding portion of the first suture can be positioned over an upper surface of the third pad. In some instances, the third pad can be positioned between the first pad and the second pad. In some instances, the first pad, the second pad, and the third pad can be evenly distributed around the opening in the target tissue along the first path.

The second suture can be coupled to the third pad. The second suture can comprise a corresponding portion positioned over the third pad. In some instances, the corresponding portion of the second suture positioned over the third pad can be parallel or substantially parallel to the third corresponding portion of the first suture positioned over the third pad.

In some instances, a fourth pad can be coupled to the first suture. The fourth pad can be positioned over the target tissue at a fourth position on the first path. The fourth pad can be positioned between the third pad and the second pad. In some instances, the first pad, the second pad, the third pad and the fourth pad can be evenly distributed around the opening in the target tissue along the first path. A fourth corresponding portion of the first suture can be positioned over an upper surface of the fourth pad. The second suture can be coupled to the fourth pad. The second suture can comprise a corresponding portion positioned over the fourth pad. In some instances, the corresponding portion of the second suture positioned over the fourth pad can be parallel or substantially parallel to the fourth corresponding portion of the first suture positioned over the third pad.

FIG. 12 shows another example of process 1200 for suturing a first purse-string suture and a second purse-string suture around an opening in a target tissue. A first suture can be used to form the first purse-strong suture and a second suture can be used to form the second purse-string suture. At block 1202, the process 1200 can involve threading the first suture through a first location on a first pad from an upper surface to a lower surface of the first pad, and threading the first suture through a second location on the first pad from the upper surface to the lower surface of the first pad. A first corresponding portion of the first suture can be positioned over the upper surface of the first pad. The first location and the second location on the first pad can be less than about 2 millimeters (mm) from respective nearest edges of the first pad. For example, the first location and the second location can be less than about 2 millimeters (mm) from a respective opposing edge of the first pad. The first suture can run along a path less than about 2 millimeters (mm) from a nearest edge of the first pad, such as an edge perpendicular or substantially perpendicular to the opposing edges.

At block 1204, the process 1200 can involve positioning the first pad over the target tissue at a first position along the first path for forming the first purse-string suture around the opening in the target tissue.

At block 1206, the process 1200 can involve threading the first suture through the target tissue along the first path from the first position on the first path to a second position on the first path.

At block 1208, the process 1200 can involve threading a first distal portion of the first suture through a first location on a second pad from a lower surface of the second pad to an upper surface of the second pad.

At block 1210, the process 1200 can involve threading a second distal portion of the first suture through a second location on the second pad from the lower surface of the second pad to the upper surface of the second pad. The first location and second location on the second pad can be less than about 2 millimeters from respective nearest edges of the second pad, including from a respective opposing edge of the second pad. In some instances, the first and second locations can be less than about 2 millimeters (mm) from a third edge of the second pad, such as an edge perpendicular or substantially perpendicular to the opposing edges.

At block 1212, the process 1200 can involve positioning the second pad over the target tissue at the second position on the first path.

At block 1214, the process 1200 can involve threading the second suture through a first location from an upper surface to a lower surface of one of the first pad and the second pad, and threading the second suture through a second location from the upper surface to the lower surface of the one of the first pad and the second pad. A first corresponding portion of the second suture can be positioned over the upper surface of the one of the first pad and the second pad. In some instances, the first location and the second location on the one of the first pad and the second pad can be less than about 2 millimeters (mm) from respective nearest edges of the pad, such as a respective opposing edge of the pad. The second suture can run along a path less than about 2 millimeters (mm) from a nearest edge of the one of the first pad and the second pad, such as an edge perpendicular or substantially perpendicular to the opposing edges.

At block 1216, the process 1200 can involve threading a first distal portion of the second suture through a first location from a lower surface to an upper surface of the other of the first pad and the second pad and threading a second distal portion of the second suture through a second location from the lower surface to the upper surface of the other of the first pad and the second pad. The first and second locations on the other of the first pad and the second pad can be less than about 2 millimeters (mm) from respective nearest edges of the pad, including from a respective opposing edge. The first and second locations can be less than about 2 millimeters (mm) from an edge perpendicular or substantially perpendicular to the opposing edges.

At block 1218, the process 1200 can involve tensioning the first suture to form the first purse-string suture and tensioning the second suture to form the second purse-string suture. In some instances, the first distal portion and the second distal portion of the first suture can be tensioned. In some instances, the first distal portion of the second suture and second distal portion of the second suture can be tensioned.

In some instances, the first pad and the second pad can be positioned at opposing locations around the opening. In some instances, the first purse-string suture and the second purse-string suture can be coupled to two pads such that the first and second pad are positioned at opposing locations along the first path and the second path.

In some instances, the first purse-string suture and the second purse-string suture can comprise more than two pads coupled thereto. For example, a third pad can be coupled to the first and second purse-string sutures. In some instances, the third pad can be positioned over the target tissue at a third position around the target opening. The first suture can be threaded through the target tissue from the first position to the third position on the first path. The third pad can be coupled to the third pad. For example, a third corresponding portion of the first suture, such as a third pad portion of the first suture, can be positioned over the upper surface of the third pad, where the upper surface of the third pad can be configured to be oriented away from the target tissue. The first suture can be threaded through a first location on the third pad from a lower surface to the upper surface of the third pad, and through a second location on the third pad from the upper surface to the lower surface of the third pad. The first and second locations can be less than about 2 millimeters (mm) from respective nearest edges of the third pad, such as a respective opposing edge of the third pad. The first suture can run along a path less than about 2 millimeters (mm) from a nearest edge of the third pad, such as an edge perpendicular or substantially perpendicular to the opposing edges. In some instances, the first pad, the second pad and the third pad can be evenly distributed around the opening in the target tissue, for example being positioned along the first path and second path at equal distances from the nearest two pads.

The second suture can be coupled to the third pad. A corresponding portion of the second suture can be positioned over the upper surface of the third pad. For example, the second suture can be threaded through a third location on the third pad from the lower surface to the upper surface of the third pad, and through a fourth location on the third pad from the upper surface to the lower surface of the third pad to position the corresponding portion of the second suture over the upper surface of the third pad. The third and fourth locations can be less than about 2 millimeters (mm) from respective nearest edges of the third pad, such as a respective opposing edge of the third pad. The second suture can run along a path less than about 2 millimeters (mm) from a nearest edge of the third pad, such as an edge perpendicular or substantially perpendicular to the opposing edges.

In some instances, a fourth pad can be coupled to the first purse-string suture and second purse-string suture. For example, the fourth pad can be positioned at predetermined position around the opening along the first path, such as at a fourth position between the third pad and the second pad. In some instances, coupling the fourth pad can comprise threading the first suture through the target tissue from the third position to a fourth position on the first path. In some instances, the first suture can be threaded through a first location on the fourth pad from a lower surface to an upper surface of the fourth pad, and through a second location on the fourth pad from the upper surface to the lower surface of the fourth pad, to position a fourth corresponding portion of the first suture over the upper surface of the fourth pad.

The second suture can be coupled to the fourth pad. In some instances, the second suture can be threaded through a third location from the lower surface to the upper surface of the fourth pad, and through a fourth location from the upper surface to the lower surface of the fourth pad to position a corresponding portion of the second suture over the upper surface of the fourth pad. The third and fourth locations can be less than about 2 millimeters (mm) from respective nearest edges of the fourth pad, such as a respective opposing edge of the fourth pad. The second suture can run along a path less than about 2 millimeters (mm) from a nearest edge of the fourth pad, such as an edge perpendicular or substantially perpendicular to the opposing edges. In some instances, the first pad, the second pad, the third pad, and the fourth pad can be evenly distributed around the opening along the first path.

Additional Instances

Depending on the instance, certain acts, events, or functions of any of the processes or algorithms described herein can be performed in a different sequence, may be added, merged, or left out altogether. Thus, in certain instances, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain instances include, while other instances do not include, certain features, elements and/or steps. Thus, such conditional language is not generally intended to imply that features, elements and/or steps are in any way required for one or more instances or that one or more instances necessarily include logic for deciding, with or without author input or prompting, whether these features, elements and/or steps are included or are to be performed in any particular instance. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain instances require at least one of X, at least one of Y and at least one of Z to each be present.

It should be appreciated that in the above description of instances, various features are sometimes grouped together in a single instance, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular instance herein can be applied to or used with any other instance(s). Further, no component, feature, step, or group of components, features, or steps are necessary or indispensable for each instance. Thus, it is intended that the scope of the inventions herein disclosed and claimed below should not be limited by the particular instances described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example instances belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of suturing an opening in a target tissue, the method comprising:
    positioning a first pad over a target tissue at a first position on a first path for forming a first purse-string suture around the opening in the target tissue, the first pad being coupled to a first suture, wherein a first corresponding portion of the first suture is over an upper surface of the first pad, and wherein the upper surface of the first pad is configured to be oriented away from the target tissue;
    coupling a first distal portion of the first suture and a second distal portion of the first suture to a second pad;
    positioning the second pad at a second position on the first path;
    providing a second suture coupled to one of the first pad and the second pad, the second suture for forming a second purse-string suture in the target tissue along a second path around and concentric with the first path, wherein a first corresponding portion of the second suture is over an upper surface of the one of the first pad and the second pad, and wherein the upper surface of the one of the first pad and the second pad is configured to be oriented away from the target tissue;
    coupling a first distal portion of the second suture and a second distal portion of the second suture to the other of the first pad and the second pad; and
    tensioning the first distal portion and second distal portion of the first suture to form the first purse-string suture, and tensioning the first distal portion of the second suture and second distal portion of the second suture to form the second purse-string suture.

2. The method of claim 1, wherein ends of the first corresponding portion of the first suture positioned over the upper surface of the first pad are less than about 2 millimeters (mm) from respective nearest edges of the first pad.

3. The method of claim 1, wherein coupling the first distal portion and the second distal portion of the first suture to the second pad comprises coupling the first distal portion and the second distal portion to respective locations on the second pad which are less than about 2 millimeters (mm) from respective nearest edges of the second pad.

4. The method of claim 1, wherein the target tissue is heart tissue and wherein positioning the first pad comprises positioning the first pad over a pericardium and at an apex region of a heart and aligning the first pad with a posterior mitral leaflet direction.

5. The method of claim 1, wherein positioning the second pad comprises positioning the second pad at an opposing location from that of the first pad along the first path.

6. The method of claim 1, wherein distal ends of the first corresponding portion of the second suture positioned over the upper surface of the one of the first pad and the second pad are less than about 2 millimeters (mm) from respective nearest edges of the one of the first pad and the second pad.

7. The method of claim 1, wherein coupling the first distal portion and the second distal portion of the second suture to the other of the first pad and the second pad comprises coupling the first distal portion and the second distal portion to respective locations on the other of the first pad and the second pad which are less than about 2 millimeters (mm) from respective nearest edges the first pad or the second pad.

8. The method of claim 1, further comprising positioning a third pad over the target tissue at a third position on the first path, the third pad being coupled to the first suture and a third corresponding portion of the first suture being over an upper surface of the third pad, wherein the upper surface of the third pad is configured to be oriented away from the target tissue.

9. The method of claim 8, wherein positioning the third pad over the target tissue at the third position comprises positioning the third pad between the first pad and the second pad.

10. The method of claim 8, wherein positioning the first pad, positioning the second pad, and positioning the third pad comprises evenly distributing the first pad, the second pad, and the third pad around the opening in the target tissue along the first path.

11. The method of claim 8, wherein distal ends of the third corresponding portion of the first suture positioned over the third pad are less than about 2 millimeters (mm) from respective nearest edges of the third pad.

12. The method of claim 8, further comprising coupling the second suture to the third pad, the second suture comprising a third corresponding portion positioned over the third pad, and the third corresponding portion of the second suture being parallel to the third corresponding portion of the first suture.

13. The method of claim 12, wherein distal ends of the third corresponding portion of the second suture positioned over the third pad are less than about 2 millimeters (mm) from respective nearest edges of the third pad.

14. The method of claim 12, further comprising positioning a fourth pad over the target tissue at a fourth position on the first path, the fourth pad being coupled to the first suture and a fourth corresponding portion of the first suture being over an upper surface of the fourth pad, wherein the upper surface of the fourth pad is configured to be oriented away from the target tissue.

15. The method of claim 14, wherein positioning the fourth pad over the target tissue at the fourth position comprises positioning the fourth pad between the third pad and the second pad.

16. The method of claim 14, wherein positioning the first pad, positioning the second pad, positioning the third pad, and positioning the fourth pad comprises evenly distributing the first pad, the second pad, the third pad and the fourth pad around the opening in the target tissue along the first path.

17. The method of claim 14, wherein distal ends of the fourth corresponding portion of the first suture positioned over the fourth pad are less than about 2 millimeters (mm) from respective nearest edges of the fourth pad.

18. The method of claim 14, further comprising coupling the second suture to the fourth pad, the second suture comprising a fourth corresponding portion over the fourth pad.

19. The method of claim 14, wherein distal ends of the fourth corresponding portion of the second suture over the fourth pad are less than about 2 millimeters (mm) from respective nearest edges of the fourth pad.

20. The method of claim 1, wherein the first pad and the second pad each comprise a pledget.

* * * * *